(12) United States Patent
Deppermann et al.

(10) Patent No.: US 10,542,661 B2
(45) Date of Patent: *Jan. 28, 2020

(54) AUTOMATED HIGH-THROUGHPUT SEED SAMPLER AND METHODS OF SAMPLING, TESTING AND BULKING SEEDS

(71) Applicant: Monsanto Technology LLC, St. Louis, MO (US)

(72) Inventors: Kevin L. Deppermann, St. Charles, MO (US); Lee Yannakakis, Chesterfield, MO (US); Andrew M. Singleton, Manchester, MO (US); Angela R. Cargill, St. Louis, MO (US); David W. Finley, St. Louis, MO (US); Brian J. Forinash, St. Louis, MO (US); Allen N. Ondes, St. Louis, MO (US); Sam R. Eathington, St. Louis, MO (US); Heather M. Forbes, St. Charles, MO (US); Bruce J. Schnicker, Wildwood, MO (US); Jason K. Bull, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/411,531

(22) Filed: Jan. 20, 2017

(65) Prior Publication Data

US 2017/0196161 A1    Jul. 13, 2017

Related U.S. Application Data

(63) Continuation of application No. 14/635,738, filed on Mar. 2, 2015, now Pat. No. 9,551,636, which is a
(Continued)

(51) Int. Cl.
*A01C 1/02* (2006.01)
*A01C 1/00* (2006.01)
(Continued)

(52) U.S. Cl.
CPC ............. *A01C 1/025* (2013.01); *A01C 1/00* (2013.01); *C12Q 1/6895* (2013.01); *G01N 1/04* (2013.01);
(Continued)

(58) Field of Classification Search
CPC ................. A01C 1/00; A01C 1/025
(Continued)

(56) References Cited

U.S. PATENT DOCUMENTS

| | | |
|---|---|---|
| 2,502,809 A | 4/1950 | Vogelsang |
| 2,756,903 A | 7/1956 | Kreidler |

(Continued)

FOREIGN PATENT DOCUMENTS

| | | |
|---|---|---|
| CL | 1035-03 | 5/2003 |
| CL | 2189-05 | 8/2005 |

(Continued)

OTHER PUBLICATIONS

Anklam et al., Analytical methods for detection and determination of genetically modified organisms in agricultural crops and plant-derived food products. (Eur Food Res Technol. 214:3-26), Jan. 2002, 24 pages.

(Continued)

*Primary Examiner* — Monica L Williams
(74) *Attorney, Agent, or Firm* — James E. Davis; Harness, Dickey & Pierce, P.L.C.

(57) ABSTRACT

An automated method for analyzing seeds generally includes collecting image data from individual seeds using a seed sampling system, determining at least one characteristic of each of the individual seeds based on the collected
(Continued)

image data, and removing tissue from each of the individual seeds using the seed sampling system. The method also includes, prior to removing the tissue sample from each of the individual seeds, adjusting at least one operational parameter of the seed sampling system based on the at least one characteristic of the seed from which the tissue is to be removed to thereby allow for generally consistent removal of tissue from each of the individual seeds. In some aspects, the method further includes analyzing the tissue removed from the seeds for presence or absence of at least one characteristic, and selecting seeds based on presence or absence of the at least one characteristic.

19 Claims, 23 Drawing Sheets

Related U.S. Application Data continuation of application No. 13/897,024, filed on May 17, 2013, now Pat. No. 8,997,398, which is a continuation of application No. 13/556,742, filed on Jul. 24, 2012, now Pat. No. 8,443,545, which is a continuation of application No. 13/251,993, filed on Oct. 3, 2011, now Pat. No. 8,245,439, which is a continuation of application No. 12/128,279, filed on May 28, 2008, now Pat. No. 8,028,469, which is a continuation-in-part of application No. 11/680,180, filed on Feb. 28, 2007, now Pat. No. 7,998,669.

(60) Provisional application No. 60/940,788, filed on May 30, 2007, provisional application No. 60/778,830, filed on Mar. 2, 2006.

(51) Int. Cl.
*G01N 1/04* (2006.01)
*G01N 15/14* (2006.01)
*G01N 1/28* (2006.01)
*C12Q 1/6895* (2018.01)
*G01N 24/08* (2006.01)
*G01N 15/00* (2006.01)

(52) U.S. Cl.
CPC .............. *G01N 1/28* (2013.01); *G01N 1/286* (2013.01); *G01N 15/1459* (2013.01); *G01N 15/1463* (2013.01); *C12Q 2600/13* (2013.01); *G01N 24/08* (2013.01); *G01N 2015/0019* (2013.01); *G01N 2015/149* (2013.01); *G01N 2015/1497* (2013.01)

(58) Field of Classification Search
USPC .................................................. 47/58.1 SE
See application file for complete search history.

(56) References Cited

U.S. PATENT DOCUMENTS

| | | |
|---|---|---|
| 3,350,372 A | 10/1967 | Anspon et al. |
| 3,530,372 A | 9/1970 | Laukien |
| 3,642,128 A | 2/1972 | Westwood et al. |
| 3,852,914 A | 12/1974 | Levengood |
| 3,861,788 A | 1/1975 | Webster |
| 4,037,970 A | 7/1977 | Webster et al. |
| 4,040,747 A | 8/1977 | Webster |
| 4,260,262 A | 4/1981 | Webster |
| 4,278,183 A | 7/1981 | Billington |
| 4,305,130 A | 12/1981 | Kelley |
| 4,375,854 A | 3/1983 | Hedel |
| 4,465,017 A | 8/1984 | Simmons |
| 4,480,765 A | 11/1984 | Tonus |
| 4,654,592 A | 3/1987 | Zens |
| 4,734,584 A | 3/1988 | Rosenthal |
| 4,752,689 A | 6/1988 | Satake |
| 4,818,380 A | 4/1989 | Azegami et al. |
| 4,884,696 A | 12/1989 | Peleg |
| 4,931,061 A | 6/1990 | Young |
| 4,946,046 A | 8/1990 | Affleck et al. |
| 5,051,699 A | 9/1991 | Hanawa |
| 5,132,538 A | 7/1992 | Norris |
| 5,221,518 A | 6/1993 | Mills |
| 5,245,188 A | 9/1993 | Satake et al. |
| 5,253,302 A | 10/1993 | Massen |
| 5,412,220 A | 5/1995 | Moore |
| 5,475,221 A | 12/1995 | Wang |
| 5,533,145 A | 7/1996 | Shofner et al. |
| 5,590,791 A | 1/1997 | Gschweitl |
| 5,668,374 A | 9/1997 | DiFoggio et al. |
| 5,669,511 A | 9/1997 | Satake et al. |
| 5,733,592 A | 3/1998 | Wettstein et al. |
| 5,751,421 A | 5/1998 | Wright et al. |
| 5,764,819 A | 6/1998 | Orr |
| 5,833,947 A | 11/1998 | Rocklage |
| 5,836,438 A | 11/1998 | Jung |
| 5,837,458 A | 11/1998 | Minshull et al. |
| 5,864,984 A | 2/1999 | McNertney |
| 5,918,977 A | 7/1999 | Borggaard et al. |
| 5,991,025 A | 11/1999 | Wright et al. |
| 6,100,526 A | 8/2000 | Mayes |
| 6,150,158 A | 11/2000 | Bhide et al. |
| 6,237,286 B1 | 5/2001 | Williames |
| 6,266,864 B1 | 7/2001 | Barber |
| 6,307,123 B1 | 10/2001 | Kriz et al. |
| 6,397,678 B1 | 6/2002 | Popper |
| 6,537,826 B1 | 3/2003 | Horigane |
| 6,646,264 B1 | 11/2003 | Modiano et al. |
| 6,705,827 B2 | 3/2004 | Keller et al. |
| 6,706,989 B2 | 3/2004 | Hunter et al. |
| 6,782,991 B2 | 8/2004 | Johansson |
| 6,809,819 B1 | 10/2004 | Vinjamoori et al. |
| 6,879,389 B2 | 4/2005 | Meyer et al. |
| 6,947,144 B2 | 9/2005 | Kim et al. |
| 6,959,617 B2 | 11/2005 | Deppermann |
| 7,044,306 B2 | 5/2006 | Deppermann |
| 7,067,834 B2 | 6/2006 | Horigane et al. |
| 7,367,155 B2 | 5/2008 | Kotyk et al. |
| 7,502,113 B2 | 3/2009 | Deppermann et al. |
| 7,591,101 B2 | 9/2009 | Deppermann |
| 7,600,642 B2 | 10/2009 | Deppermann |
| 7,611,842 B2 | 11/2009 | Deppermann et al. |
| 7,685,768 B2 | 3/2010 | Deppermann |
| 7,703,238 B2 | 4/2010 | Deppermann et al. |
| 7,767,883 B2 | 8/2010 | Deppermann et al. |
| 7,830,516 B2 | 11/2010 | Deppermann et al. |
| 7,832,143 B2 | 11/2010 | Deppermann et al. |
| 7,849,632 B2 | 12/2010 | Deppermann et al. |
| 7,877,926 B2 | 2/2011 | Deppermann |
| 7,941,969 B2 | 5/2011 | Deppermann et al. |
| 7,998,669 B2 | 8/2011 | Deppermann et al. |
| 8,028,469 B2 | 10/2011 | Deppermann et al. |
| 8,071,845 B2 | 12/2011 | Deppermann et al. |
| 8,189,901 B2 | 5/2012 | Modiano et al. |
| 8,245,439 B2 | 8/2012 | Deppermann et al. |
| 8,312,672 B2 | 11/2012 | Deppermann et al. |
| 8,401,271 B2 | 3/2013 | Deppermann et al. |
| 8,434,259 B2 | 5/2013 | Deppermann |
| 8,436,225 B2 | 5/2013 | Deppermann et al. |
| 8,443,545 B2 | 5/2013 | Deppermann et al. |
| 8,501,480 B2 | 8/2013 | Deppermann et al. |
| 8,539,713 B2 | 9/2013 | Deppermann et al. |
| 8,548,222 B2 | 10/2013 | Deppermann et al. |
| 8,561,346 B2 | 10/2013 | Deppermann et al. |
| 8,959,833 B2 | 2/2015 | Deppermann et al. |
| 8,965,101 B2 | 2/2015 | Deppermann et al. |
| 8,997,398 B2 | 4/2015 | Deppermann et al. |
| 9,003,696 B2 | 4/2015 | Deppermann |
| 9,027,278 B2 | 5/2015 | Deppermann et al. |
| 9,275,265 B2 | 3/2016 | Deppermann et al. |
| 9,383,291 B2 | 7/2016 | Deppermann et al. |
| 9,551,636 B2 | 1/2017 | Deppermann et al. |

(56) References Cited

U.S. PATENT DOCUMENTS

| | | | |
|---|---|---|---|
| 9,986,699 B2 | 6/2018 | Deppermann et al. | |
| 2001/0013486 A1 | 8/2001 | Yamakawa | |
| 2001/0014750 A1 | 8/2001 | Ulrich et al. | |
| 2001/0024796 A1 | 9/2001 | Selifonov et al. | |
| 2002/0070150 A1 | 6/2002 | Keller et al. | |
| 2002/0144458 A1 | 10/2002 | Hunter et al. | |
| 2003/0142852 A1 | 7/2003 | Lu et al. | |
| 2003/0188998 A1 | 10/2003 | Deppermann | |
| 2004/0072143 A1 | 4/2004 | Timmis | |
| 2004/0074822 A1 | 4/2004 | Horigane et al. | |
| 2004/0141641 A1 | 7/2004 | McDonald et al. | |
| 2004/0160607 A1 | 8/2004 | Lin et al. | |
| 2004/0221335 A1 | 11/2004 | Shewmaker et al. | |
| 2004/0247756 A1 | 12/2004 | Imura | |
| 2005/0082207 A1 | 4/2005 | Deppermann | |
| 2005/0097021 A1 | 5/2005 | Behr et al. | |
| 2005/0114918 A1 | 5/2005 | Hirahara et al. | |
| 2005/0154221 A1 | 7/2005 | Lysenko et al. | |
| 2006/0042527 A1 | 3/2006 | Deppermann | |
| 2006/0042528 A1 | 3/2006 | Deppermann | |
| 2006/0046244 A1 | 3/2006 | Deppermann | |
| 2006/0046264 A1 | 3/2006 | Deppermann et al. | |
| 2006/0048247 A1 | 3/2006 | Deppermann | |
| 2006/0048248 A1 | 3/2006 | Deppermann | |
| 2006/0112628 A1 | 6/2006 | Kotyk et al. | |
| 2007/0048872 A1 | 3/2007 | Deppermann et al. | |
| 2007/0204366 A1 | 8/2007 | Deppermann et al. | |
| 2007/0207485 A1 | 9/2007 | Deppermann et al. | |
| 2007/0240242 A1 | 10/2007 | Modiano et al. | |
| 2008/0000815 A1 | 1/2008 | Deppermann | |
| 2008/0113367 A1 | 5/2008 | Becker et al. | |
| 2008/0131254 A1 | 6/2008 | Cope et al. | |
| 2008/0131924 A1 | 6/2008 | Cope et al. | |
| 2008/0310674 A1 | 12/2008 | Modiano et al. | |
| 2008/0317279 A1 | 12/2008 | Deppermann et al. | |
| 2009/0032441 A1 | 2/2009 | Corak et al. | |
| 2009/0155878 A1 | 6/2009 | Becker et al. | |
| 2010/0263087 A1 | 10/2010 | Deppermann et al. | |
| 2010/0299790 A1 | 11/2010 | Deppermann et al. | |
| 2011/0081716 A1 | 4/2011 | Deppermann | |
| 2011/0129836 A1 | 6/2011 | Deppermann et al. | |
| 2011/0217700 A1 | 9/2011 | Deppermann et al. | |
| 2011/0296930 A1 | 12/2011 | Deppermann et al. | |
| 2012/0021411 A1 | 1/2012 | Deppermann et al. | |
| 2012/0117865 A1 | 5/2012 | Deppermann et al. | |
| 2012/0180386 A1 | 7/2012 | Deppermann et al. | |
| 2012/0228199 A1 | 11/2012 | Modiano et al. | |
| 2012/0288854 A1 | 11/2012 | Deppermann et al. | |
| 2013/0244321 A1 | 9/2013 | Deppermann | |
| 2013/0260366 A1 | 10/2013 | Deppermann et al. | |
| 2015/0164011 A1 | 6/2015 | Deppermann et al. | |
| 2015/0165484 A1 | 6/2015 | Deppermann et al. | |
| 2015/0241322 A1 | 8/2015 | Deppermann et al. | |
| 2015/0355205 A1 | 12/2015 | Deppermann et al. | |
| 2016/0313220 A1 | 10/2016 | Deppermann et al. | |
| 2017/0003201 A1 | 1/2017 | Deppermann | |

FOREIGN PATENT DOCUMENTS

| | | |
|---|---|---|
| CL | 2190-05 | 8/2005 |
| CL | 573-07 | 3/2007 |
| CN | 2510248 | 9/2002 |
| DE | 198 45 883 A1 | 5/1999 |
| DE | 10 2004 063769 | 7/2006 |
| EP | 0 127 313 | 7/1989 |
| EP | 0 636 310 | 2/1995 |
| EP | 0 730 164 | 9/1996 |
| EP | 0 750 188 | 12/1996 |
| EP | 0 511 184 | 6/1998 |
| EP | 0 539 537 | 12/2000 |
| EP | 1 126 268 A1 | 8/2001 |
| EP | 1 401 589 | 1/2003 |
| EP | 1 786 261 | 5/2007 |
| EP | 1 862 051 | 12/2007 |
| EP | 1 991 043 | 5/2010 |
| EP | 2 279 658 | 2/2011 |
| FR | 2549963 | 1/1985 |
| GB | 1151988 | 5/1969 |
| GB | 1355612 | 6/1974 |
| GB | 1408458 | 10/1975 |
| GB | 1471076 | 4/1977 |
| JP | 406284806 A | 10/1994 |
| JP | 10-319106 | 12/1998 |
| JP | 2000055910 A | 2/2000 |
| RU | 2126618 C1 | 2/1999 |
| RU | 2267766 C1 | 1/2006 |
| SU | 1446521 | 12/1989 |
| SU | 1658858 | 6/1991 |
| SU | 1805835 | 3/1993 |
| UA | 91985 | 8/2005 |
| WO | WO 96/24830 | 8/1996 |
| WO | WO 97/00887 | 1/1997 |
| WO | WO 98/14046 | 4/1998 |
| WO | WO 98/44140 | 10/1998 |
| WO | WO 99/40419 | 8/1999 |
| WO | WO 99/41383 | 8/1999 |
| WO | WO 99/58959 | 11/1999 |
| WO | WO 00/52990 | 9/2000 |
| WO | WO 00/71993 | 11/2000 |
| WO | WO 2001/022043 | 3/2001 |
| WO | WO 01/44828 | 6/2001 |
| WO | WO 01/89288 | 11/2001 |
| WO | WO 02/16090 | 2/2002 |
| WO | WO 02/048687 | 6/2002 |
| WO | WO 02/059586 | 8/2002 |
| WO | WO 2002/071040 | 9/2002 |
| WO | WO 03/100381 | 12/2003 |
| WO | WO 2004/063333 | 7/2004 |
| WO | WO 2005/031367 | 4/2005 |
| WO | WO 2006/026466 | 3/2006 |
| WO | WO 2006/026467 | 3/2006 |
| WO | WO 2007/025250 | 3/2007 |
| WO | WO 2007/103769 | 9/2007 |
| WO | WO 2008/150798 | 12/2008 |
| WO | WO 2012/012411 | 1/2012 |

OTHER PUBLICATIONS

Archibald et al., "Development of Short-Wavelength Near-Infrared Spectral Imaging for Grain Color Classification," SPIE vol. 3543, pp. 189-198 (1998).

Arumuganathan, K. & Earle, E.D., *Estimation of Nuclear DNA Content of Plants by Flow Cytometry*, Plant Molecular Biology Reporter 9(3):229-241 (1991).

Bauman et al., Inheritance of Variations in Oil Content of Individual Corn (*Zea mays* L.) Kernels, Crop Science, 5:137-138 (1965).

Benito et al., Rapid identification of Triticeae genotypes from single seeds using the polymerase chain reaction, Plant Molecular Biology 21:181-183, 1993, 3 pages.

Bor-Yaw Lin, Ploidy Barrier to Endosperm Development in Maize (Genetics 107:103-115), May 1984, 13 pages.

Brumback, Jr., et al., "Automating fatty acid analyses from seeds: from field samples to data bases," Lab. Inf. Manage., 21 (1993) pp. 215-222.

Chenault et al., A Non-destructive Seed Sampling Method for PCR-based Analyses in Marker Assisted Selection and Transgene Screening, Peanut Science, 34:38-43 (2007).

Chunwongse J., et al., "Pre-germination genotyping screening using PCR amplification of half-seeds", Theoretical and Applied Genetics, Springer, Berlin, DE, vol. 86, No. 6, Jan. 1993, pp. 694-698.

Churchill, F., *William Johannsen and the Genotype Concept*, Journal of the History of Biology, 7(1):5-30 (1974).

Concibido, V.C. et al., *Introgression of a quantitative trait locus for yield from Glycine soja into commercial soybean cultivars*, Theor. Appl. Genet. 106:575-582 (2003).

Dahmer et al., "A Rapid Screening Technique for Determining the Lipid Composition of Soybean Seeds", Journal of the American Oil Chemists' Society, Springer, Berlin, DE, vol. 66, Jan. 1989, pp. 543-549.

(56) References Cited

OTHER PUBLICATIONS

Daun et al., "Comparison of Three Whole Seed Near-Infrared Analyzers for Measuring Quality Components of Canola Seed", JAOCS, 71(10):1063-1068 (1994).
Delwiche, "Single Wheat Kernel Analysis by Near-Infrared Transmittance: Protein Content," Analytical Techniques and Instrumentation, JAOCS, 72(1):11-16 (1995).
Demidov Dimitri et al., "Additive effects of the feed-back insensitive bacterial aspartate kinase and the Brazil nut 2S albumin on the methionine content of transgenic narbon bean (*Vicia narbonensis* L.).", Molecular Breeding, vol. 11, No. 3, Apr. 2003, pp. 187-201.
Dowell et al., "Automated Single Wheat Kernel Quality Measurement Using Near-Infrared Reflectance," *ASAE Annual International Meeting*, paper No. 973022 (1997).
Dowell et al., "Automated Color Classification of Single Wheat Kernels Using Visible and Near-Infrared Reflectance," *Cereal Chem* 75(1):142-144 (1998).
Dowell, "An Intelligent Automated System for Determining Peanut Quality," *IEEE International Workshop on Intelligent Robots and Sytems, IROS*, pp. 237-241 (1990).
Dr. Jolanta Soos, "Industrial Process Monitoring Requires Rugged AOTF Tools", Laser Focus World, Aug. 1994.
Eder, J. & Chalyk, S., In vivo *haploid induction in maize*, Theor. Appl. Genet., 104:703-708 (2002).
Frisch, M. et al., *Comparison of Selection Strategies for Marker-Assisted Backcrossing of a Gene*, Crop Science 39:1295-1301 (1999).
Gambhir et al. "Simultaneous Determination of Moisture and Oil Content in Oilseeds by Pulsed Nuclear Magnetic Resonance," JAOCS, 62(1):103-108 (1985).
Gao et al., Development of a seed DNA-based genotyping system for marker-assisted selection in maize, Moi Breeding, 22:477-494 (2008).
Gao et al., Revisiting the Hetero-Fertilization Phenomenon in Maize, PLoS One, vol. 6, Issue 1, Jan. 2011, 7 pages.
Gillaspie, Jr., "Sensitive Method for Testing Peanut Seed Lots for Peanut Stripe and Peanut Mottle Viruses by Immunocapture-Reverse Transcription-Polymerase Chain Reaction", Plant Disease, May 2000, pp. 559-561.
Groos, C. et al., *Study of the relationship between pre-harvest sprouting and grain color by quantitative trait loci analysis in a white red grain bread-wheat cross*, Theor. Appl. Genet. 104:39-47 (2002).
Halloin et al. "Proton Magnetic Resonance Imaging of Lipid in Pecan Embryos," JAOCS, 70(12):1259-1262 (1993).
He, L. & Wang, K., *A 384-Well Microtiter-Plate-Based Template Preparation and Sequencing Method*, PCR Cloning Protocols 411-416 (2nd. ed., Humana Press 2002).
Heil et al. "Magnetic Resonance Imaging and Modeling of Water Up-take into Dry Beans," *Lebensm-Wiss-u-Technol*, 25:280-285 (1992).
Higley P M et al., "Evaluation of Seed Biopsy Methods for Nondestructive Seed Health Testing", Phytopathology, St. Paul, MN, US, vol. 79, No. 10, Jan. 1989, p. 1140.
Horigane et al., *Two-dimensional analysis of kernels using a new sample preparation method*, Chemistry and Biology, 41(6):398-402, Jun. 25, 2003 (Published in Japanese—an English language translation is included).
Horigane, A. et al., *Evaluation of Color Characteristics of Cross-Sectioned Wheat Kernels*, Food Science & Technology Research 9(4):327-331 (2003).
J.P. Hazebroek, "Analysis of genetically modified oils" Progress in Lipid Research 39 (2000) pp. 477-506.
Jones D A L M Barber et al., "An analysis of seed development in Pisum sativum L. XVI. Assessing variation for fatty acid content by use of a non-destructive technique for single-seed analysis", Plant Breeding, vol. 114, No. 1, 1995, pp. 81-83.
Jousse et al., Rapid, cost-effective screening of flax genotypes to identify desirable fatty acid compositions, Electronic Journal of Plant Breeding, 1(6):1396-1404 (2010).
Kamiya et al., Rapid DNA Extraction Method from Soybean Seeds, Breeding Science 53:277-279 (2003).
Kang et al., A Rapid DNA Extraction Method for RFLP and PCR Analysis from a Single Dry Seed, Plant Molecular Biology Reporter, 16:1-9 (1998).
Karcz Jagna et al., "Structural and embryological studies of diploid and tetraploid *Arabidopsis thaliana* (L.) Heynah", Acta Biologica Cracoviensia Series Botanica, vol. 42, No. 2, 2000, pp. 113-124.
Kato, A., *Chromosome doubling of haploid maize seedlings using nitrous oxide gas at the flower primordial stage*, Plant Breeding 121:370-377 (2002).
Kisha, T.J. et al., *Genetic Diversity among Soybean Plant Introductions and North American Germplasm*, Crop Science 38:1669-1680 (1998).
Kotyk et al., High-Throughput Determination of Oil Content in Corn Kernels Using Nuclear Magnetic Resonance Imaging, JAOCS, vol. 82, No. 12, 2005, pp. 855-862.
Kramer et al., "Transgenic Avidin Maize is Resistant to Storage Insect Pests", Nature Biotechnology, vol. 18, Jun. 2000, pp. 670-674.
Krisnangkura K. et al., "Continuous transmethylation of palm oil in an organic solvent", Jaoch, vol. 69, 1992.
Kristensen, H. and Aastrup, S., A non-destructive screening method for proanthocyanidin-free barley mutants, Carlesberg Res. Commun. 51 (1986) 509-513.
Krysan, "Breakthrough Technologies, Ice-Cap. A High-Throughput Method for Capturing Plant Tissue Samples for Genotype Analysis", Plant Physiology, Jul. 2004 vol. 135, pp. 1162-1169.
Lakshminarayana et al. "Spatial distribution of oil in groundnut and sunflower seeds by nuclear magnetic resonance imaging," *J. Biosci* 17(1):87-93 (1992).
Li et al., Molecular Mapping Genes Conditioning Reduced Palmitic Acid Content in N87-2122-4 Soybean (Crop Science 42:373-378), 2002, 6 pages.
Lipman et al., *Tolerance of Liquid-Air Temperature by Seeds of Higher Plants for Sixty Days*, Plant Physiology 392-394 (1934).
MacNamara et al., "Multiplex sample NMR: an approach to high-throughput NMR using a parallel coil probe," *Analytica Chimica Acta*, 397:9-16 (1999).
Manabe et al., Segregation distortion through female gametophates in interspecific hybrids of tetraploid wheat as revealed by RAPD analysis (Hereditas 131: 47-53), Oct., 1999, 7 pages.
Massie, et al. "Spectral Reflectance and Transmittance Properties of Grain in the Visible and near Infrared", Transactions of the ASAE, Winter Meeting of the American Society of Agricultural Engineers, pp. 598-600 (1965).
McCarthy, Paul L., et al., "Rapid identification of transformed wheat using a half-seed PCR assay", Biotechniques, vol. 31, No. 3, Mar. 2002, pp. 560-564.
McEntyre et al., "Comparison of Water Absorption Patterns in Two Barley Cultivars, Using Magnetic Resonance Imaging," *Cereal Chem.*, 75(6):792-795 (1998).
McGinty et al. "A System for Automatic Weight Determination of Individual Grain Kernels: Principles and Evaluation," *Cereal Chem.* 19(5):196-199 (1974).
Meru et al., A non-destructive genotyping system from a single seed for marker-assisted selection in watermelon, Gmr Genetics and Molecular Research 12(1):702-709 (2013).
Notice of Opposition to European Patent EP 1869961 (Application No. EP07016960.2) as filed by Syngenta Crop Protection AG on Oct. 25, 2012, and related filings, 52 pages.
Notice of Opposition to European Patent EP 1991043 (Application No. 07757774.0) as filed by Syngenta Crop Protection AG, 29 pages, Feb. 18, 2011.
Notice of Opposition to European Patent EP 2279657 (Application No. EP10184375.3) as filed by Syngenta Crop Protection AG on Dec. 6, 2013, 21 pages.
Notice of Third Party Observations filed in European Patent EP 1869961 (Application No. EP07016960.2) Dec. 14, 2012, 11 pages.
Orman, et al. "Comparison of Near-Infrared Spectroscopy Calibration Methods for the Prediction of Protein, Oil, and Starch in Maize Grain," *J. Agric. Food Chem.* 39:883-886 (1991).

(56) References Cited

OTHER PUBLICATIONS

P.A. Hailey, "The Role of NIR Spectroscopy in the Measurement of Pharmaceutical Manufacture", http://wwwbrimrose.com/hailey.html; (Jan. 2, 2002).
Paige et al. "Apparatus for Automatic Measurement of Kernel Weight, Length, and Thickness," *Crop Sci.* 31:1314-1318 (1991).
Petition for Inter Partes Review of U.S. Pat. No. 7,832,143 as filed by E.I. du Pont de Nemours and Company on Jan. 8, 2014, 70 pages, (and 24 Exhibits).
Petition for Inter Partes Review of U.S. Pat. No. 8,028,469 as filed by E.I. du Pont de Nemours and Company on Jan. 8, 2014, 51 pages, (and 25 Exhibits).
Petition for Inter Partes Review of U.S. Pat. No. 8,071,845 as filed by E.I. du Pont de Nemours and Company on Jan. 8, 2014, 60 pages, (and 25 Exhibits).
Petition for Inter Partes Review of U.S. Pat. No. 8,245,439 as filed by E.I. du Pont de Nemours and Company on Jan. 8, 2014, 69 pages, (and 27 Exhibits).
Petition for Inter Partes Review of U.S. Pat. No. 8,312,672 as filed by E.I. du Pont de Nemours and Company on Jan. 8, 2014, 71 pages, (and 34 Exhibits).
Pioneer Hi-Bred International, Inc., Downloadable Photos—Laser-Assisted Seed Selection, http://www.pioneer.com/web/site/portal/menuiteam.b9e99dcb8e2cfd8ecfe6d10093a0/, printed as of Nov. 25, 2008, 4 pages.
Preliminary Opinion of Opposition Division relating to Opposition of European Patent EP 1869961 (Application No. EP07016960.2), Dec. 20, 2013, 11 pages.
R.K. Downey, Genetic Control of Fatty Acid Biosynthesis in Rapeseed (*Brassica napus* L.) (AOCS 41:475-478), 1964, 4 pages.
R.K. Downey, Methods of Breeding for Oil Quality in Rape (Canadian Journal of Plant Science 43:271-275), Jul. 1963, 7 pages.
Rapid identification of organic contaminants in pretreated waste water using AOTF near-IR spectrometry, ISA 1995 Meeting Proceedings, pp. 87-95 (1995).
Robutti, "Maize Kernel Hardness Estimation in Breeding by Near-Infrared Transmission Analysis," *Cereal Chem* 72(6): 632-636 (1995).
Rubel et al. "Simultaneous Determination of Oil and Water Contents in Different Oilseeds by Pulsed Nuclear Magnetic Resonance," *JAOCS* 71(10):1057-1062 (1994).
Saito et al. "Application of Magnetic Resonance Imaging to Non-Destructive Void Detection in Watermelon," *Cryogenics* 36(12):1027-1031 (1996).

Sander et al., "System for Automatic Weight Determination of Individual Grain Kernels," *Transactions of the ASAE*, pp. 1146-1147 (1973).
Sangtong, V. et al., *Serial Extraction of Endosperm Drillings (SEED)—A Method for Detecting Transgenes and Proteins in Single Viable Maize Kernels,* Plant Molecular Biology Reporter, 19:151-158 (2001).
Schuster Ivan et al., "Correlation between high molecular weight gluten subunits composition and bread-making quality in Brazilian wheat", Brazilian Journal of Genetics, vol. 20, No. 4, Dec. 1997, pp. 667-671.
Seed Meister Luminar 3076, Brimrose Corporation of America, Baltimore, MD, http://www.brimrose.com/seed_meister.html; (Jan. 3, 2002).
Siebenmorgen et al. "A Data Acquisition/Control System for Individual Kernel and Thin-Layer Grain Drying Research" *Am. Soc. of Agri. Engrs., Univ. of Ark.,* 1991 Int'l Summer Meeting, Paper 91-3042, pp. 1-16 (1991).
Smith et al., "Genetic Purity and Testing Technologies for Seed Quality: A Company Perspective", Seed Science Research, 1998, vol. 8, pp. 285-293.
Song et al., "Non-invasive Measurement of Moisture Distribution in Individual Wheat Kernels by Magnetic Resonance Imaging," *SPIE*, 2345:414-422 (1994).
Tanksley et al., Seed Banks and Molecular Maps: Unlocking Genetic Potential from the Wild (Science 277:1063-1066) Aug. 1997, 5 pages.
Van Der Mey J A M et al., "Mass Screening for Alkaloid Content in Lupinus-Albus", Applied Plant Science, vol. 1, No. 2, 1987, pp. 80-82.
Varshney et al., Plant Biotechnology and Molecular Markers (Kluwer Academic Publishers; Print ISBN: 1-4020-1911-4; Edited by P.S. Srivastava, Alka Narula, Sheela Srivastava) (Chapter 20), Apr. 2004, 42 pages.
Von Post, R., von Post, L., Dayteg, C., Nisson, M., Forster, B.P., and Tuvesson, S., A high-throughput DNA extraction method for barley seed. Euphytica 130 (2003) 255-260.
Wright, H., *Commercial Hybrid Seed Production,* Hybridization of Crop Plants 161-176 (1980).
Yoshida et al., "An automatic sequential single-seed weighing system: variation in soybean seed weight," *J. Fac. Agr. Hokkido Univ.* 61(2):225-232 (1982).
Zeile, W.L. et al., "A Rapid Non-Destructive Technique for Fatty Acid Determination in Individual Peanut Seed" Peanut Science (1993) 20:9-11 (3 pages).

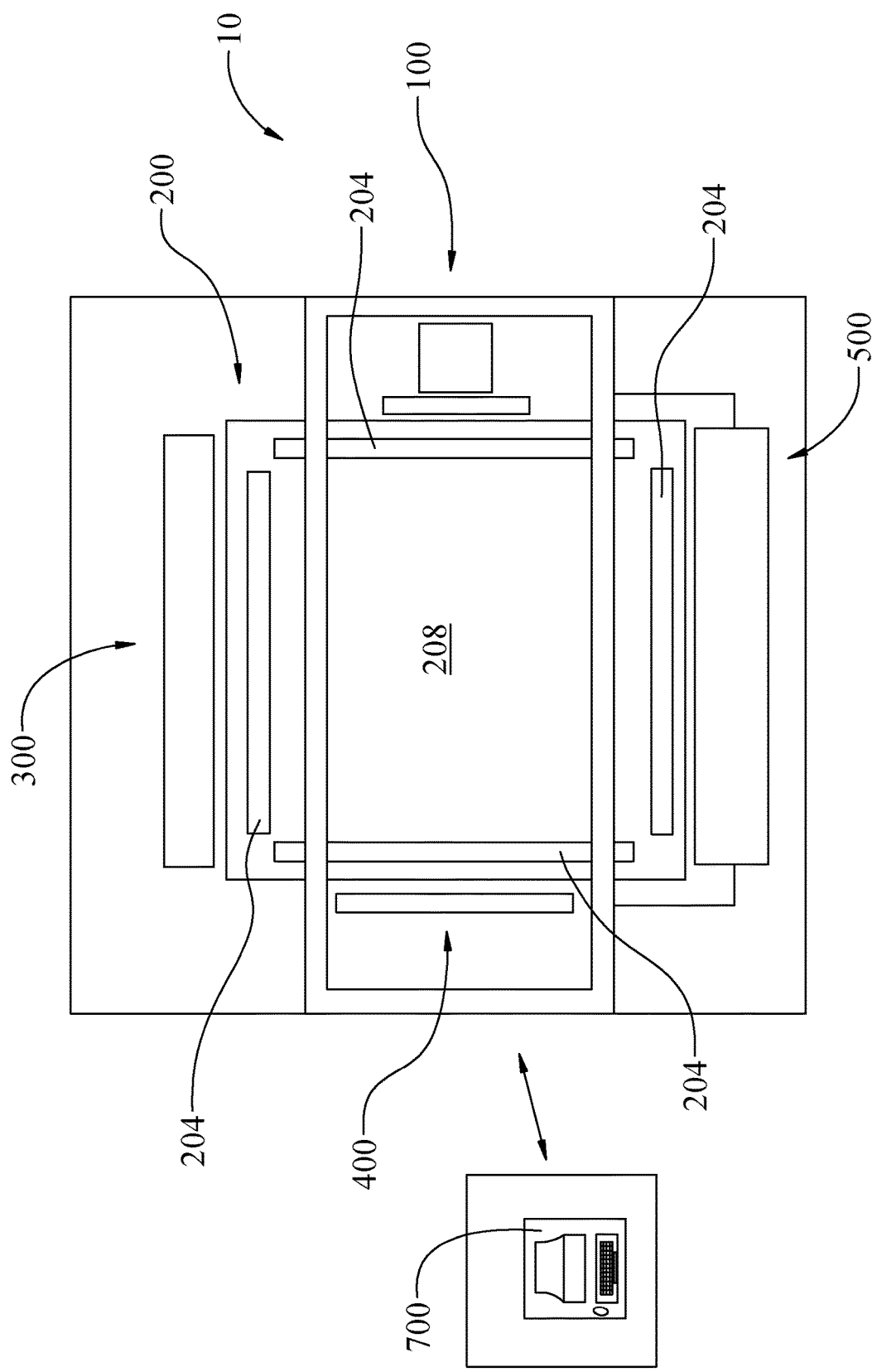

AUTOMATED HIGH-THROUGHPUT SEED SAMPLER AND METHODS OF SAMPLING, TESTING AND BULKING SEEDS

CROSS-REFERENCE TO RELATED APPLICATIONS

This application is a continuation of U.S. patent application Ser. No. 14/635,738, filed Mar. 2, 2015, which is a continuation of U.S. patent application Ser. No. 13/897,024 (U.S. Pat. No. 8,997,398), filed May 17, 2013, which is a continuation of U.S. patent application Ser. No. 13/556,742 (U.S. Pat. No. 8,443,545), filed Jul. 24, 2012, which is a continuation of U.S. patent application Ser. No. 13/251,993 (U.S. Pat. No. 8,245,439), filed Oct. 3, 2011, which is a continuation of U.S. patent application Ser. No. 12/128,279 (U.S. Pat. No. 8,028,469), filed May 28, 2008. U.S. patent application Ser. No. 12/128,279 claims the benefit of U.S. Provisional Application Ser. No. 60/940,788, filed May 30, 2007, and is also a continuation-in-part of U.S. patent application Ser. No. 11/680,180 (U.S. Pat. No. 7,998,669), filed Feb. 28, 2007, which claims the benefit of U.S. Provisional Application Ser. No. 60/778,830, filed Mar. 2, 2006. The entire disclosures of each of the above applications are incorporated herein by reference.

FIELD

This disclosure generally relates to systems and methods for taking samples from biological materials such as seeds.

BACKGROUND

The statements in this section merely provide background information related to the present disclosure and may not constitute prior art.

In plant development and improvement, genetic improvements are made in the plant, either through selective breeding or genetic manipulation, and when a desirable improvement is achieved, a commercial quantity is developed by planting and harvesting seeds over several generations. Not all seeds express the desired traits and, thus, these seeds need to be culled from the population. To hasten the process of bulking up the population, statistical samples are taken and tested to cull seeds from the population that do not adequately express the desired trait.

U.S. patent application Ser. No. 11/680,180 (filed Feb. 28, 2007); U.S. patent application Ser. No. 11/213,430 (filed Aug. 26, 2005); U.S. patent application Ser. No. 11/213,431 (filed Aug. 26, 2005); U.S. patent application Ser. No. 11/213,432 (filed Aug. 26, 2005); U.S. patent application Ser. No. 11/213,434 (filed Aug. 26, 2005); U.S. patent application Ser. No. 11/213,435 (filed Aug. 26, 2005); U.S. patent application Ser. No. 11/680,180 (filed Feb. 27, 2007); and U.S. patent application Ser. No. 11/680,611 (filed Feb. 27, 2007), which are incorporated herein by reference in their entirety, disclose apparatus and systems for the automated sampling of seeds as well as methods of sampling, testing and bulking seeds.

SUMMARY

The present disclosure relates to systems and methods of separating seeds from a plurality of seeds, extracting a sample from each seed, sorting the extracted samples and corresponding seeds respectively to wells in sample trays and seed trays, and mapping the respective wells to track each sample with the seed from which it was extracted. The methods are particularly adapted for automation, which permits a greater sampling and sorting efficiency and throughput rate than was previously practical.

In various embodiments, the present disclosure provides an automated system for sampling and sorting at least one seed from a plurality of seeds. The system includes a seed loading station for separating at least one seed from a plurality of seeds in a bulk seed hopper, an imaging station for collecting image data of the at least one seed, and a seed orientation station for independently positioning and retaining each seed in a desired orientation based on the collected image data. The system also includes a seed sample and sort station for extracting a tissue sample from each seed, sorting each tissue sample to a sample tray and sorting each sampled seed to a seed tray.

In various other embodiments, the present disclosure provides an automated, high-throughput method for extracting sample material for testing from individual seeds in a population of seeds. The method includes separating at least one seed from a plurality of seeds in a population, collecting image data from the at least one seed, independently positioning the at least one seed in a desired orientation based on the collected image data, extracting a tissue sample from the at least one seed, and sorting the tissue sample to a sample tray and sorting the sampled seed to a seed tray.

In yet other various embodiments, the present disclosure provides an automated system for sequentially removing sample material from individual ones of a plurality of seeds while preserving the germination viability of the seeds. The system includes a seed loading station for separating and retaining sets of seeds from a plurality of seeds in a bulk seed hopper, an imaging station for collecting image data of the retained sets of seeds, and a seed orientation station for independently positioning each seed in each seed set in a desired orientation based on the collected image data. The system also includes a seed sample and sort station for extracting a tissue sample from each seed in each seed set, sorting each tissue sample to a sample tray and sorting each sampled seed to a seed tray.

In still yet other various embodiments, the present disclosure provides an automated, high-throughput method for sequentially extracting sample material for testing from a plurality of seeds while preserving the germination viability of the seeds. The method includes separating sets of seeds from a plurality of seeds in a bulk seed hopper. Each set of seeds is then presented for retention by a respective one of a plurality of rotary vacuum cup banks at a seed loading station of a seed sampling and sorting system. Each rotary vacuum cup bank includes a plurality of rotary vacuum cup devices. The method additionally includes collecting image data of each set of seeds retained by each rotary vacuum cup bank at an imaging station of the seed sampling and sorting system. The method further includes independently positioning each seed in the set in a desired orientation based on the collected image data at a seed orientation station of the seed sampling and sorting system. The method still further includes extracting a sample from each seed in each set of seeds; and sorting each sample to a sample tray and sorting each sampled seed to a seed tray at a seed sample and sort station of the seed sampling and sorting system.

In still other various embodiments, the present disclosure provides a seed loading station of an automated seed sampling and sorting system. The seed loading station includes a separating wheel for separating seeds from a plurality of seeds in a bulk hopper. Additionally, the seed loading station includes a tube shuttle having a plurality of first transfer tubes extending from a plurality of openings in the tube shuttle. The tube shuttle is structured and operable to incrementally positioning each of the first transfer tubes under the separating wheel such that each of the first transfer tubes receives a seed from the separating wheel.

In other various embodiments, the present disclosure provides a seed sample and sort station of an automated seed sampling and sorting system. The seed sample and sort station includes a press plate bank including a number of press plates equal to a number of seed retention devices of an automated seed sampling and sorting system. Each seed retention device retains a respective seed. The seed sample and sort station additionally includes a linear actuator to which the press plate bank is mounted. The linear actuator is controllable to lower the press plate bank such that each press plate engages a friction plate of a corresponding one of the retention devices and moves the respective seeds downward to a sampling location. The seed sample and sort station further includes a plurality of independently controlled grip and chip assemblies. Each grip and chip assembly includes a seed gripping mechanism for firmly holding a respective one of the seeds at the respective sampling location as a sample is extracted from the respective seed. Each grip and chip assembly additionally includes a sample extraction mechanism for extracting the sample from each respective seed.

In still other embodiments, methods are provided for removing tissue from multiple individual seeds. In one example embodiment, a method for removing tissue from multiple individual seeds generally includes loading multiple individual seeds in a seed transport, orienting the multiple individual seeds in the seed transport substantially simultaneously, and removing tissue from the oriented multiple individual seeds.

In another example embodiment, an automated method for sampling seeds includes separating individual seeds from a plurality of seeds, imaging the separated seeds, and removing tissue samples from the imaged seeds.

In other embodiments, seed sampling systems are provided. In one example embodiment, a seed sampling system generally includes a seed transport configured to hold multiple individual seeds together as a group and transport the multiple individual seeds together as the group, and to allow the multiple individual seeds to be oriented while the multiple individual seeds are being held in the seed transport; and a seed sampling subsystem configured to remove tissue from the oriented multiple individual seeds.

In another example embodiment, an automated system for sampling seeds includes a seed loading station for separating individual seeds from a plurality of seeds held in a seed hopper, an imaging station configured to receive the separated seeds from the seed loading station and collect image data of the received seeds, and a seed sampling subsystem configured to remove tissue samples from the seeds after the image data of the seeds is collected.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 2 is a block diagram of a top view of the seed sampling system shown in FIG. 1.

DETAILED DESCRIPTION

Figure 1:
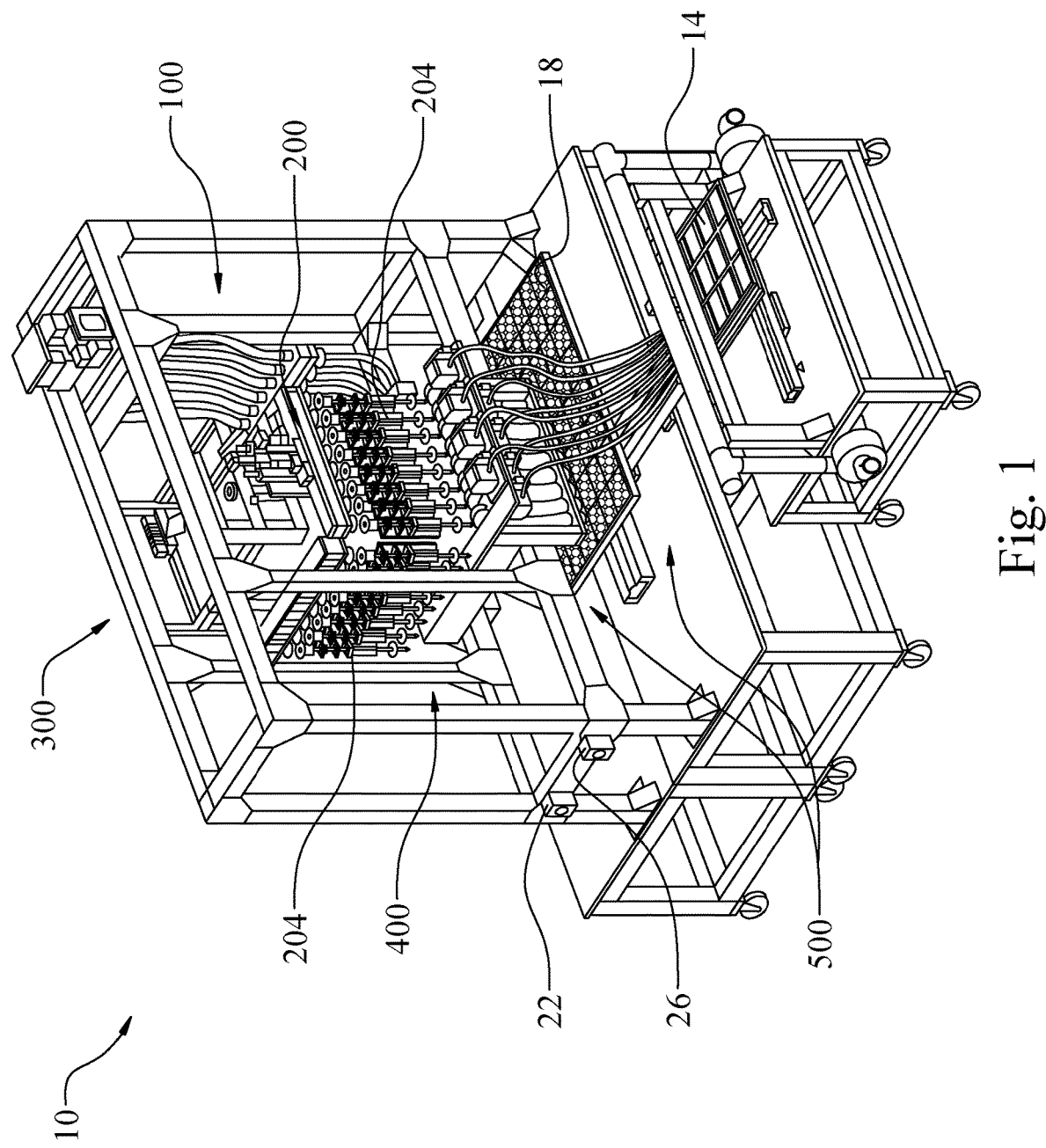
FIG. 1 is an isometric view of a seed sampling system in accordance with various embodiments of the present disclosure.

The following description is merely exemplary in nature and is in no way intended to limit the present teachings, application, or uses. Throughout this specification, like reference numerals will be used to refer to like elements.

FIGS. 1 and 2 illustrate an automated seed sampling system 10, in accordance with various embodiments of the present disclosure. The seed sorter system 10 includes a seed loading station 100, a seed transport subsystem 200, a seed imagining station 300, a seed orientation station 400, a seed sampling and sort station 500 and a central controller system (CCS) 700 that controls the operation of the seed sorter system 10.

Generally, the seed sampling system 10 is structured and operable to repetitiously separate a select number of seeds, e.g., sets of eight seeds at a time, from a bulk of seeds within a bulk seed hopper 104 (e.g., FIG. 3A, etc.) at the seed loading station 100. Additionally, the seed sampling system 10 is structured and operable to image each set of seeds at the imaging station 300. The images collected at the imaging station 300 can be any desirable type of images. For example, the images can be visual images, near infra-red (NIR) images or NMR/MRI images, or any other type images. In various embodiments, the imaging station 300 collects at least one digital image of each set of seeds. The image data collected of each set of seeds is communicated to a CCS 700 where the image data is analyzed to determine the orientation, e.g., 'tip out' or 'crown out'. The seed sampling system 10 is further structured and operable to orient each set of seeds in a desired orientation, based on the images of each respective set of seeds, at the orientation station 400. The seed sampling system 10 is still further structured and operable to extract a sample (e.g., a tissue sample, etc.) from a selected area, e.g., the crown, of each seed in each set of seeds. Further yet, the seed sampling system 10 is structured and operable to then collect the extracted samples in a plurality of sample trays 14 and sort the respective sampled seeds into a plurality of seed trays 18 at the seed sample and sort station 500.

Once a set of seeds is separated from the bulk of seeds at the seed loading stations, as described below, the seeds are loaded onto one of a plurality of rotary vacuum cup (RVC) banks 204. The respective set of seeds is then sequentially positioned adjacent each of the imaging station 300, the orientation station 400 and the sample and sort station 500, via the seed transport subsystem 200. More specifically, the seed transport subsystem 200 includes an automated transport carousel 208 to which the plurality of the RVC banks 204 are mounted. The automated transport carousel 208 (FIG. 4A) is driven by a motor (not shown), e.g., a stepper motor, that incrementally rotates the transport carousel 208 to sequentially advance each RVC bank 204 to each of the stations 100, 300, 400 and 500. Therefore, each set of seeds is retained by a respective RVC bank 204 and transported to positions adjacent each of the imaging station 300, the orientation station 400 and the sample and sort station 500 by the incremental rotation of the transport carousel 208.

The operation of the seed sorter system 10 is generally completely controlled and automated by the CCS 700 such that the operations performed by the imaging station 300, the orientation station 400 and the sample and sort station 500 occur substantially without need for human interaction, intervention or control. However, such actions as loading the seeds into the bulk seed hopper 104 and/or physically manipulating and/or changing the sample trays 14 and seed trays 18 (either individually or collectively) can be performed manually with human participation.

Generally, the CCS 700 includes one or more processors and/or microprocessors, and one or more electronic data storage devices utilized to store and execute various custom programs, applications and/or algorithms to effectuate the operation of the seed sorter system 10. Accordingly, the CCS 700 can comprise a specially programmed computer, or computer system, in communication with associated system devices (not shown) that enable communication with and control over the operations of the various stations 100, 300, 400 and 500 and the transport subsystem 200 of the seed sorter system 10. Although the CCS 700 is exemplarily illustrated in FIG. 2 as a single unit, the CCS 700 can be a single computer based system or a plurality of computer based subsystems networked together to coordinate the simultaneous operations of the seed sorter system 10, as described herein. For example, in various embodiments, the CCS 700 can include a main controller subsystem networked together with a plurality of peripheral controller subsystems (not shown), e.g., a peripheral controller subsystem for each station 100, 300, 400, 500 and transport subsystem 200. Each peripheral controller subsystem can include one or more processors, microprocessors and electronic data storage devices that effectuate communication with various seed sorter system components, e.g., sensors, devices, mechanisms, motors, tools, etc., and together with the main controller subsystem cooperatively operate all the stations, systems and subsystems of the seed sampler system 10. Or alternatively, the CCS 700 can comprise a single computer communicatively connected to all the various system components to cooperatively operate all the stations, systems and subsystems of the seed sampler system 10.

As described above, the CCS 700 communicates with various seed sorter system components that include various system sensors. The system sensors operate to detect conditions of interest during operation of the seed sorter system 10 and communicate that information to the CCS 700. With this information, the CCS 700 generates control commands that effectuate the operations and actions taken by the various stations and components of the seed sorter system 10. For example, a sensed condition can concern: the successful isolation of sets of seeds from the seed hopper 104; the successful retention, or loading, of the each of the seeds by a respective RVC bank 204; the proper positioning of each loaded bank of seeds adjacent each respective station 300, 400 and 500; the status (for example, position, location, vacuum, pressure, and the like) of various component parts of the various stations 100, 300, 400 and 500; operation, maintenance, performance, and error feedback from the various components of each station 100, 300, 400 and 500 (separate from, or perhaps comprising or in conjunction with, collected data); and the like. More specifically, sensor information that is collected and processed for use in controlling operation of the seed sorter system 10 can include such information as: device or component status; error signals; movement; stall; position; location; temperature; voltage; current; pressure; and the like, which can be monitored with respect to the operation of each of the stations, subsystems and associated components of the seed sorter system 10.

It should be understood that the seed sorter system 10, as shown and described herein, includes various stationary braces, beams, platforms, pedestals, stands, etc., to which various components, devices, mechanisms, systems, subsystems, assemblies and sub-assemblies described herein are coupled, connected and/or mounted. Although such braces, beams, platforms, pedestals, stands, etc., are necessary to the construction of the seed sampler system 10, description of their placement, orientation and interconnections are not necessary for one skilled in the art to easily and fully comprehend the structure, function and operation of the seed sampler system 10. Particularly, such braces, beams, platforms, pedestals, stands, etc., are clearly illustrated throughout the figures and, as such, their placement, orientation and interconnections are easily understood by one skilled in the art. Therefore, for simplicity, such braces, beams, platforms, pedestals, stands, etc. will be referred to herein merely as system support structures, absent further description of their placement, orientation and interconnections.

Figure 3A:
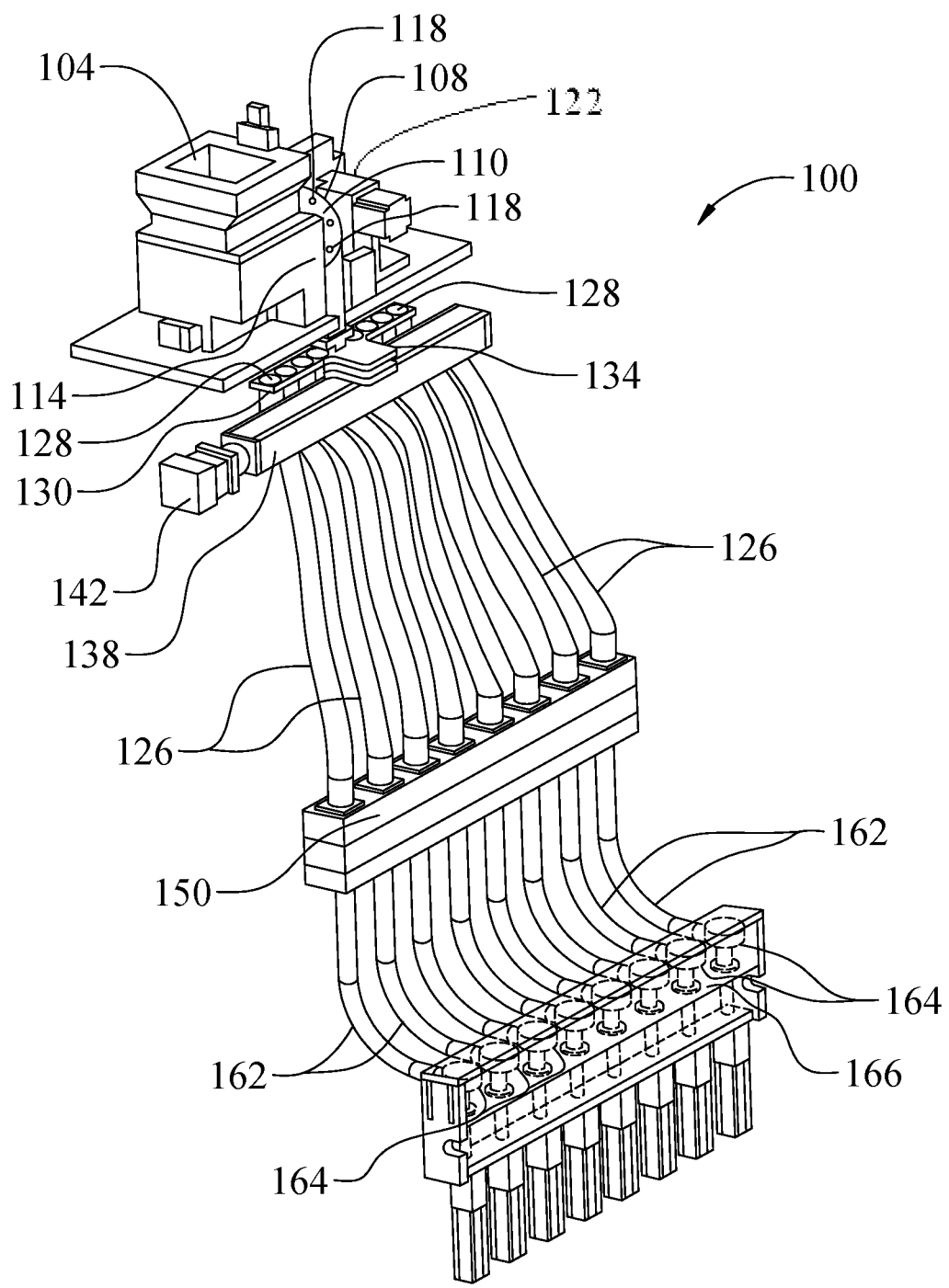
FIG. 3A is an isometric view of a seed loading station (absent system support structure) of the seed sorter system shown in FIG. 1, in accordance with various embodiments of the present disclosure.
Figure 3B:
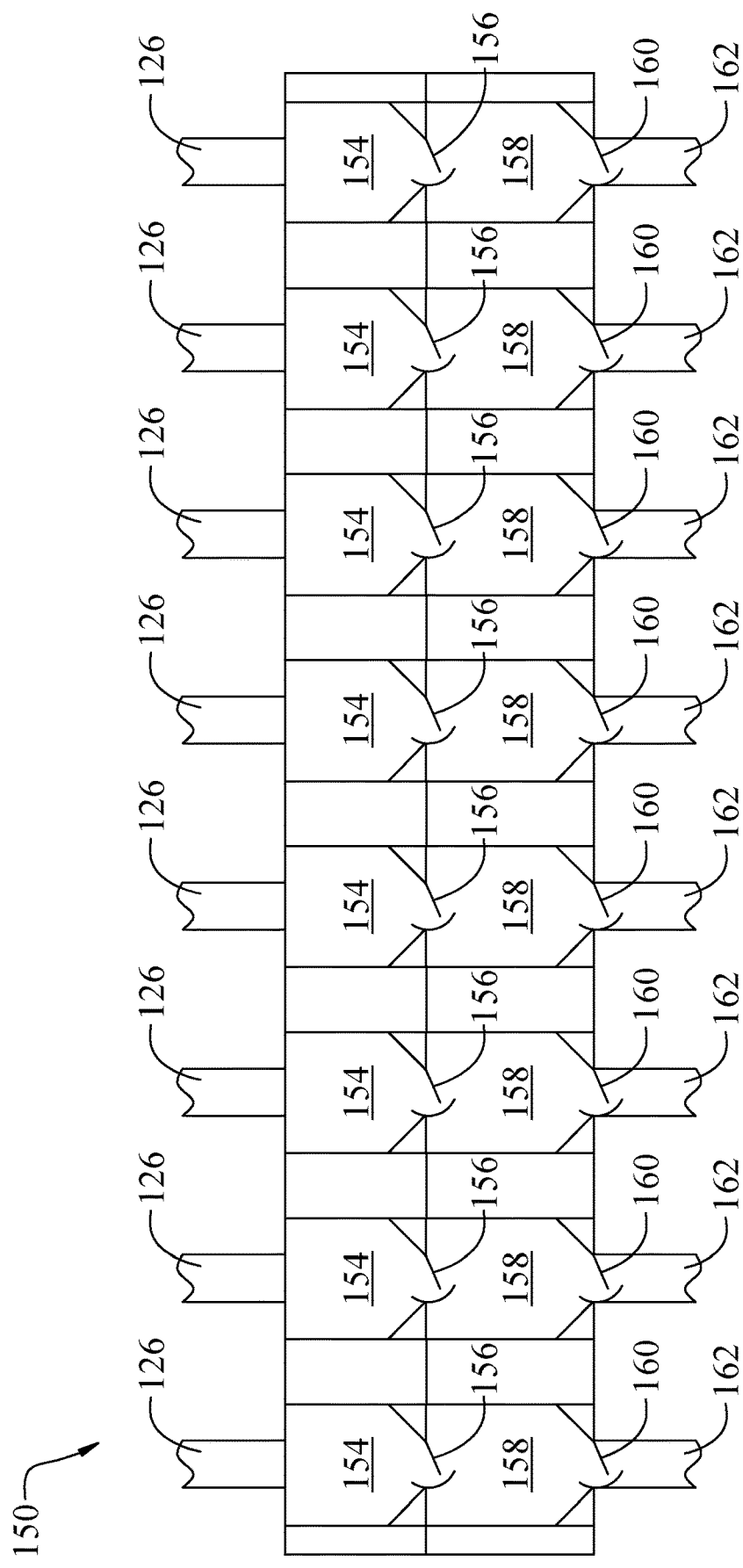
FIG. 3B is a schematic of a queuing stack of the seed loading station shown in FIG. 3A, in accordance with various embodiments of the present disclosure.
Figure 3C:
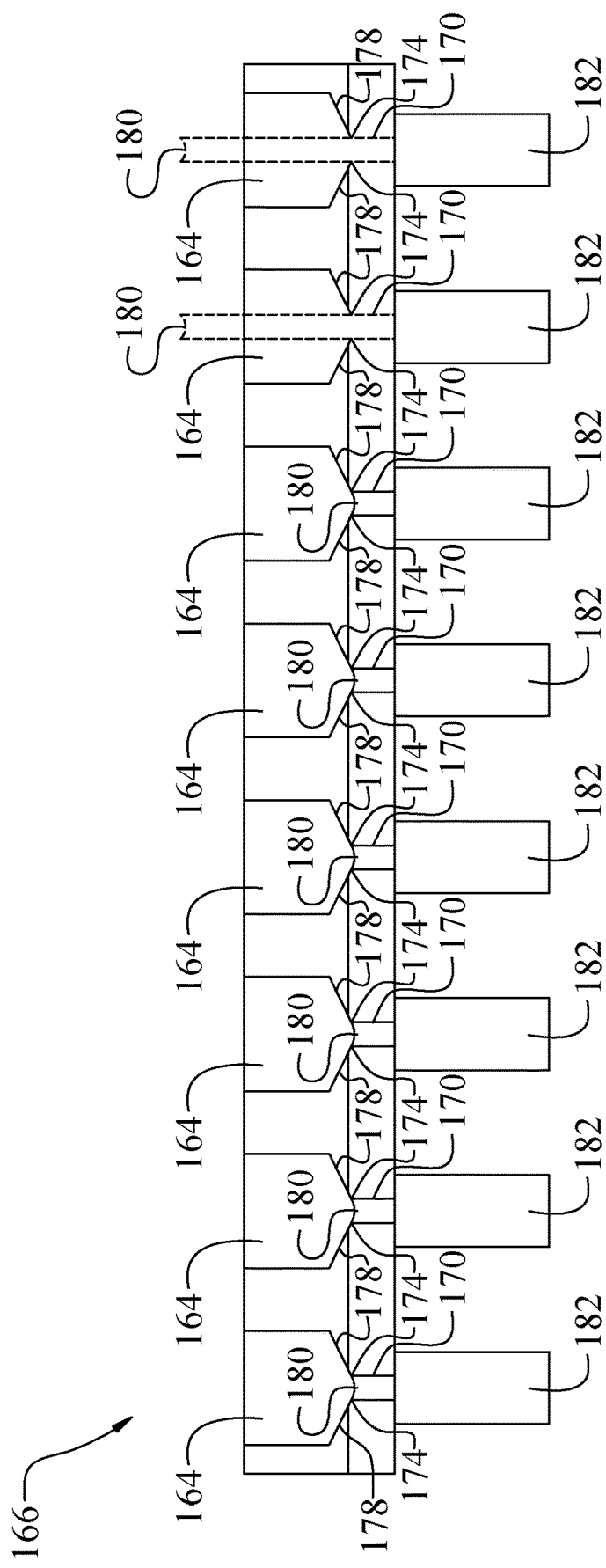
FIG. 3C is a sectional side view of an elevator hopper of the seed loading station shown in FIG. 3A, in accordance with various embodiments of the present disclosure.

Referring now to FIGS. 3A, 3B and 3C in various embodiments, the seed loading station 100 includes the seed hopper 104 and a separating wheel 108. The separating wheel 108 is mounted for rotation in a vertical plane such that a portion of the separating wheel 108 extends into an interior reservoir of the seed hopper 104. Another portion of the separating wheel 108 extends outside of the seed hopper 104 such that a face 110 of the separating wheel 108 is positioned adjacent a seed collector 114. The seed separating wheel 108 includes a plurality of spaced apart recessed ports 118 that extend through the face 110 and are communicatively coupled to a vacuum system (not shown) such that a vacuum can be provided at each of the recessed ports 118.

To initiate operation of the seed sampler system 10, seeds to be sampled and tested are placed in the seed hopper 104 interior reservoir and a vacuum is provided to at least some of the recessed ports 118, e.g., the recessed ports 118 in the face 110 of the portion of the separating wheel 108 extending into the interior reservoir of the seed hopper 104. The seed separating wheel 108 is then incrementally rotated, via an indexing motor 122, such that recessed ports 118 sequentially rotate through the interior reservoir of the seed hopper 104, out of the seed hopper 104, and past seed collector 114 before re-entering the interior reservoir of the seed hopper 104. As the separating wheel incrementally rotates and the recessed ports 118 incrementally pass through the seed hopper 104 interior reservoir, individual seeds are picked up and held at each recessed port 118 by the vacuum provided at the respective recessed ports 118. As the separating wheel 108 incrementally rotates, the seeds are carried out of the seed hopper 104 to the seed collector 114 where each seed is removed from the face 110 of the separating wheel 108.

In various embodiments, the seed collector 114 includes a wiper (not shown) that physically dislodges each seed from the respective recessed port 118 as the separating wheel 108 incrementally rotates past the seed collector 114. Alternatively, in various other embodiments, each seed can be released from respective recessed port 118 by temporarily terminating the vacuum at each individual recessed port 118 as the individual recessed port 118 is positioned adjacent the seed collector 114. In still other embodiments, each seed can be blown from the respective recessed port 118 by temporarily providing forced air at each individual recessed port 118 as the individual recessed port 118 is positioned adjacent the seed collector 114.

After each seed is removed from the separating wheel 108, the seed is funneled into one of a plurality of first transfer tubes 126 having their proximal ends connected to openings 128 in a tube shuttle 130. The tube shuttle 130 is mounted to a carriage 134 that is movably mounted to a linear translation stage 138 that includes an actuator 142 controllable by the CCS 700 to bi-directionally move the carriage 134, tube shuttle 130 and proximal ends of the first transfer tubes 126 along the translation stage 138. Therefore, as each seed is removed from the separating wheel 108, the seed is funneled into one of the first transfer tubes 126. Then the CCS 700 moves the tube shuttle 130 along the translation stage such that a subsequent first transfer tube 126 will receive the next seed removed from the separating wheel 108. This process of removing seeds is repeated until a seed has been deposited into each of the first transfer tubes 126. As each seed is removed from the separating wheel 108 and deposited into a first transfer tube 126, each seed passes through the respective first transfer tuber 126, via gravity, vacuum or forced air, to a queuing stack 150.

As shown in FIG. 3B, the queuing stack 150 includes a plurality of upper chambers 154, e.g., eight upper chambers 154. A distal end of each first transfer tube 126 terminates at a corresponding one of the upper chambers 154. Each upper chamber 154 includes an automated upper release mechanism 156, e.g., a flapper gate, that, under control of the CCS 700, retains the respective seed within the upper chamber 154. Once each upper chamber has a seed deposited therein, the upper release mechanisms 156 are commanded to release the seeds into a plurality, e.g., eight, of corresponding lower chambers 158. Similar to the upper chambers 154, each lower chamber 158 includes an automated lower release mechanism 160, e.g., a flapper gate, that, under control of the CCS 700, retains the respective seed within the lower chamber 154. The lower chambers 158 retain the seeds until such time as the CCS 700 commands the lower release mechanisms 160 to release the seeds into a plurality of corresponding second transfer tubes 162 having their proximal ends connected to the lower chambers 158.

As shown in FIG. 3C, a distal end of each second transfer tube 162 terminates at a corresponding one a plurality of elevator chambers 164, e.g., eight, of an elevator hopper 166. Thus, as the seeds are released from the lower chambers 158 into the second transfer tubes 162, each seed passes through the respective second transfer tube 162, via gravity, vacuum or forced air, into a corresponding one of the elevator chambers 164. Once a seed is deposed into each elevator chamber 164, the group of seeds therein constitutes a set of seeds, as used herein. The elevator hopper 166 additionally includes a plurality of elevator piston rods 170. Each elevator piston rod 170 is positioned within, and extendable through, an aperture 174 formed in a funnel-shaped bottom 178 of a corresponding elevator chamber 164. In various embodiments, a distal end of each elevator piston rod 170 is formed to have a concave recess 180 shaped to cradle the seeds received from the lower chambers 158 of the queuing stack 150. Additionally, the angled sides of the funnel-shaped bottom 178 allows for the seeds entering the respective elevator chambers 164 to fall onto their sides, i.e., lay flat, and be centered within the recess 180 of the respective elevator piston rods 170.

Each elevator piston rod 170 can be extended and retracted through the respective elevator chamber aperture 174 by a corresponding one of a plurality of piston actuators 182, as controlled by the CCS 700. More particularly, prior to the seeds being deposited in the elevator chambers 164, the CCS 700 commands the piston actuators 182 to retract the piston rods 170 to a retracted position where the recessed distal ends of each piston rod 170 is substantially flush with the bottom of each respective elevator chamber 164 within the respective aperture 174, as exemplarily illustrated by the six leftmost piston rods 170 in FIG. 3C. Then once the seeds are deposited into the elevator chambers 164, the seeds are retained and cradled within the respective piston rod recesses 180, until such time as the CCS 700 commands the piston actuators to extend the piston rods 170 to an extended position, as exemplarily illustrated in phantom by the two rightmost piston rods 170 in FIG. 3C. Extending the piston rods 170 raises each respective seed out of the respective elevator chamber 164 to a cued position where the set of seeds are presented for removal, processing and sampling by a RVC bank 204, as describe below.

Figure 4A:
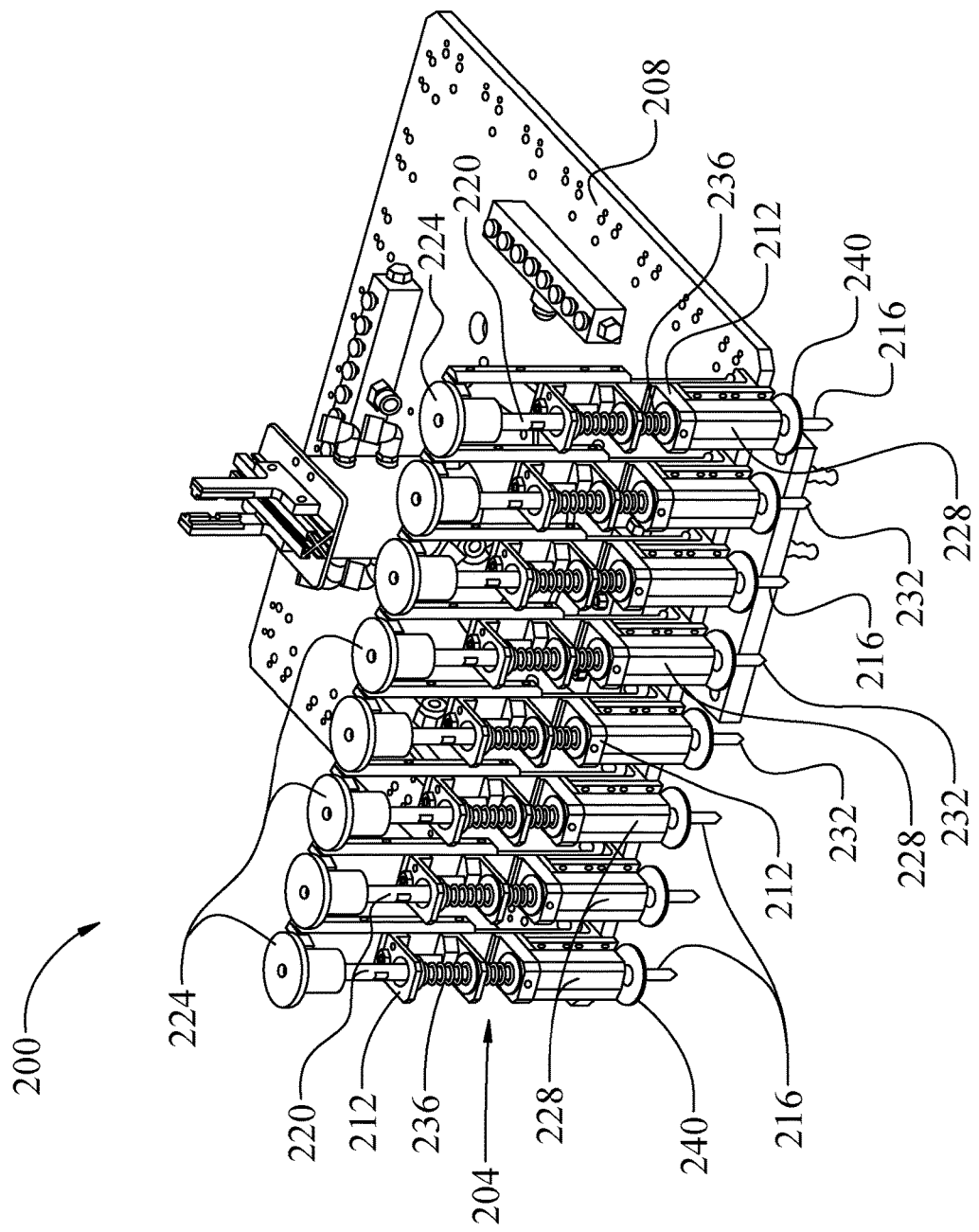
FIG. 4A is an isometric view illustrating a seed transport subsystem (absent system support structure), of the seed sorter system shown in FIG. 1, including a transport carousel having one of a plurality of rotary vacuum cup banks mounted thereto, in accordance with various embodiments of the present disclosure.
Figure 4B:
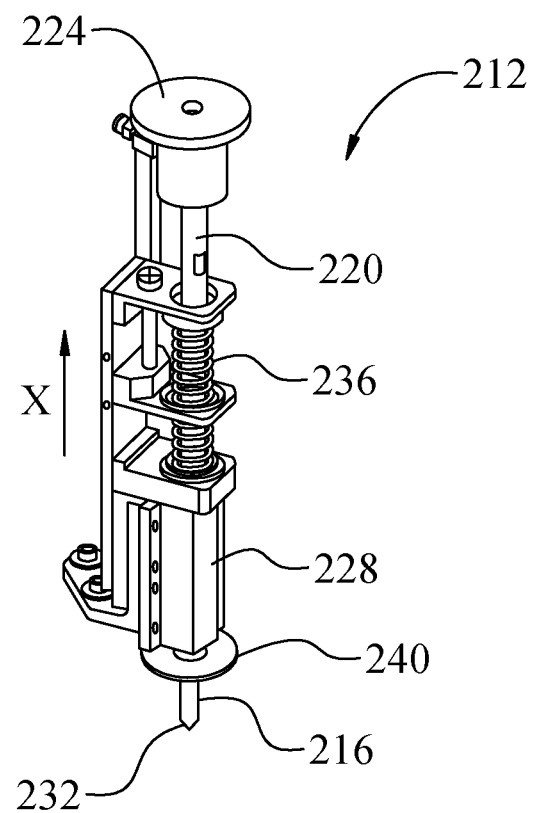
FIG. 4B is an isometric view of a rotary vacuum cup included in the rotary vacuum cup bank shown in FIG. 4A, in accordance with various embodiments of the present disclosure.

Referring now to FIGS. 4A and 4B, as described above, the seed transport subsystem 200 includes a plurality of RVC banks 204 mounted to the transport carousel 208. For simplicity and clarity, FIG. 4A illustrates a single RVC bank 204 mounted to the transport carousel 208, however, it should be understood that seed transport subsystem 200 includes a plurality of RVC banks 204 mounted thereto. For example, in various embodiments, the seed transport subsystem 200 includes four RVC banks 204, whereby each RVC bank 204 is mounted to one of four sides of the transport carousel 208. Each RVC bank includes a plurality of rotary vacuum cup (RVC) devices 212 controllable by the CCS 700 to remove a set of cued seeds from the elevator piston rods 170 and sequentially transport the respective seed set to each of the imaging station 300, the orientation station 400 and the sample and sort station 500.

Each RVC device 212 includes a vacuum cup 216 mounted to a first end of a rotary shaft 220, and a friction plate 224 mounted to an opposing second end of the rotary shaft 220. Each RVC device 212 additionally includes a shaft actuator 228 controllable by the CCS 700 to bidirectionally move the shaft 220, vacuum cup 216 and friction plate 224 along the longitudinal axis of the rotary shaft 220. That is, each actuator 228 is controlled by the CCS 700 to raise and lower the respective vacuum cup 216 as needed throughout operation of the seed sorter system 10. Each vacuum cup 216 is communicatively connected to a vacuum source (not shown) that is controlled by the CCS 700 to selectively provide a vacuum at a tip 232 of each vacuum cup 216. Each RVC device 212 further includes a biasing device 236, e.g., a spring, configured to apply a constant force on the rotary shaft 220 in the X direction. The force applied in the X direction by the biasing devices 236 maintains a locking mechanism (not shown) of each respective RVC device 212 engaged. Engagement of the locking device prevents angular rotation of the respective rotary shaft 220 and vacuum cup 216 about the longitudinal axis of the rotary shaft 220 until the locking mechanism is disengaged, as described below.

In coordination with a set of seeds being loaded into the elevator chambers 164, the CCS 700 positions an empty RVC bank 204, i.e., an RVC bank 204 without a set of seeds retained by the respective vacuum cups 216, above the elevator bank 166. The RVC devices 212 are located and mounted to the transport carousel 208, and the motor of the transport carousel 208 is controlled, such that when an RVC bank 204 is positioned adjacent the loading station 100, the vacuum cup 216 of each RVC device 212 is positioned directly above a corresponding one of the elevator chambers 164. More particularly, when an RVC bank 204 is positioned adjacent the loading station 100, the vacuum cup 216 of each RVC device 212 is positioned directly above the elevator piston rod 170 of the corresponding elevator chamber 164. Once the elevator chambers 164 are loaded with a set of seeds, and an empty RVC bank 204 is positioned adjacent the loading station 100, the CCS 700 can command the elevator piston rods 170 to raise the set of seeds to the cued position. The RVC devices 212 are further located and mounted to the transport carousel 208, such that when the elevator piston rods 170 are in the extended position, i.e., the set of seeds are cued, each seed is in light contact with, or close proximity to, the corresponding vacuum cup 216. A vacuum is then provided to each vacuum cup tip 232. The vacuum cup tips 232 are sized, and fabricated from a suitable material, such that when the vacuum is provided, each respective seed is firmly retained on the respective tip 232. The CCS 700 then retracts the elevator piston rods 170 leaving the set of seeds firmly retained on the respective vacuum cup tips 232. The retained set of seeds can then be positioned adjacent the imaging station 300, via advancement of the transport carousel 204.

Figure 5A:
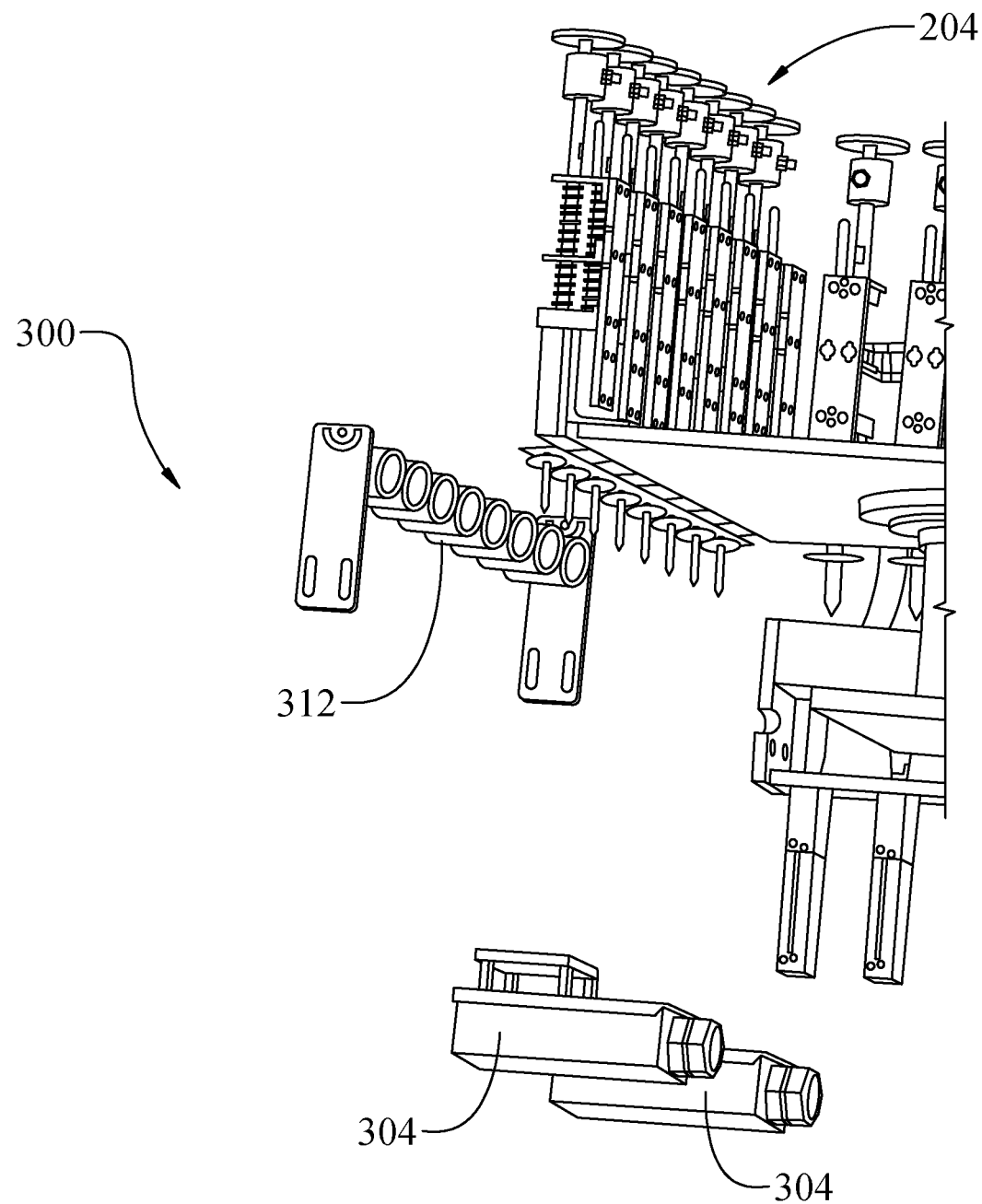
FIG. 5A is an isometric view of an imaging station (absent system support structure), of the seed sorter system shown in FIG. 1, in accordance with various embodiments of the present disclosure.
Figure 5B:
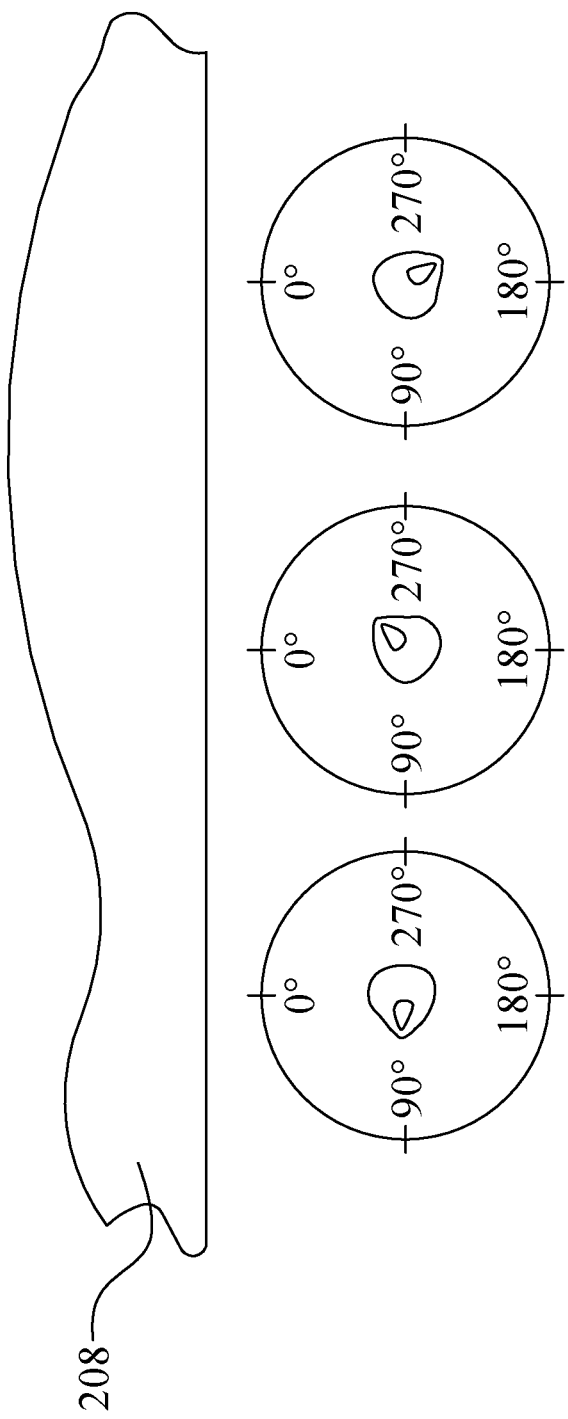
FIG. 5B is an exemplary schematic illustrating a 360° plane in which the orientation of seed tips of a plurality of seeds are determined at the imaging station shown in FIG. 5A.

Referring now to FIGS. 5A and 5B, in various embodiments, the imaging station 300 includes at least one imaging device 304 mounted to system support structure such that the one or more imaging devices 304 is/are positioned under the RVC bank 204 and the respective set of seeds when the set of seeds is advanced from the loading station 100. In various embodiments, the imaging station 300 includes a first imaging device 304 positioned and operable to collect image data for a first one-half of the seed set, and a second imaging device 304 positioned and operable to collect image data for a second one-half of the seed set. More particularly, the first imaging device 304 is mounted to the system support structure such that a field of view of the first imaging device 304 includes a bottom side of a first half of the seeds positioned adjacent the imaging station 300. And, the second imaging device 304 is mounted to the system support structure such that a field of view of the second imaging device 304 includes a bottom side of a second half of the seeds positioned adjacent the imaging station 300.

As used herein, reference to the bottom side of the seeds refers to the side of the seeds that is facing downward with respect to the orientation of each seed as retained by the respective vacuum cup 216. As described above, the shape of the elevator chamber bottoms 178 and the shape of the recesses 180 at the distal ends of each elevator rod 170 are designed such that each seed is preferably retained on the vacuum cup tips 232 by one of the opposing broad sides of each respective seed. That is, each seed is preferably held on the respective vacuum cup 216 by one of the broader sides such that germ of the seed is viewable by the imaging device(s) 304 and the tip of each seed is pointing anywhere within a 360° plane that is substantially orthogonal to the respective vacuum cup 216. The imaging device(s) 304 may be any suitable imaging device selected in accordance with the imaging goals of seed sorter system 10. For example, in connection with an analysis for external seed coat, the first imaging device 304 may comprise a digital camera operable in the visible light range. Alternatively, for internal seed analysis, the first imaging device 304 may comprise a camera operable in the near infra-red light range (see, U.S. application for patent Ser. No. 09/698,214, the disclosure of which is hereby incorporated by reference). Still further, the first imaging device 304 may comprise a camera which implements NMR/MRI imaging techniques (see, U.S. application for patent Ser. No. 09/739,871, the disclosure of which is hereby incorporated by reference).

The imaging station 300 further includes a light source 312 mounted to system support structure for illuminating the field of view of the imaging device(s) 304. The source 312 can be any type of light source suited for the particular imaging application of the seed sorter system 10. For example, the light source 312 can be one or more incandescent lights, fluorescent lights, ultraviolet lights, infrared lights, etc. In various embodiments, the light source 312 comprises a bank of light emitting diodes (LEDs), e.g., 630 nm LEDs. For example, the light source 312 comprises a bank of LEDs wherein each seed in the seed set has a corresponding LED as the primary light source illuminating the respective seed. Additionally, in various embodiments, each vacuum cup 216 includes a dark colored, e.g., black, background disk 240 (FIG. 4B) that provides a dark background for each seed during imaging and prevents image data interference from system components and structure beyond the seeds and within the field of view of imaging device(s) 304.

The image data is transmitted to the CCS 700 and stored (at least temporarily) in an electronic data storage device of the CCS 700. The CCS 700 analyzes the data to determine a directional orientation of the tip of each seed. That is, the CCS 700 analyzes the image data to determine which direction the tip of each individual seed is pointing within the 360° plane substantially orthogonal to the respective vacuum cup 216. For example, with reference to FIG. 5B, if a point on the 360° plane that is directly opposite the transfer carousel 208 is considered the origin, i.e., 0°, the CCS 700 may analyze the image data to determine that the tip one of the seeds in the seed set is oriented at 90°, while the tip of another of the seeds in the seed set is oriented at 315°, and the tip of yet another seed is oriented at 200°, etc. Once the image data of the respective seed set is collected and transmitted to the CCS 700, by the imaging device(s) 304, the transfer carousel 208 is advanced to position the seed set adjacent the orientation station 400.

Figure 6A:
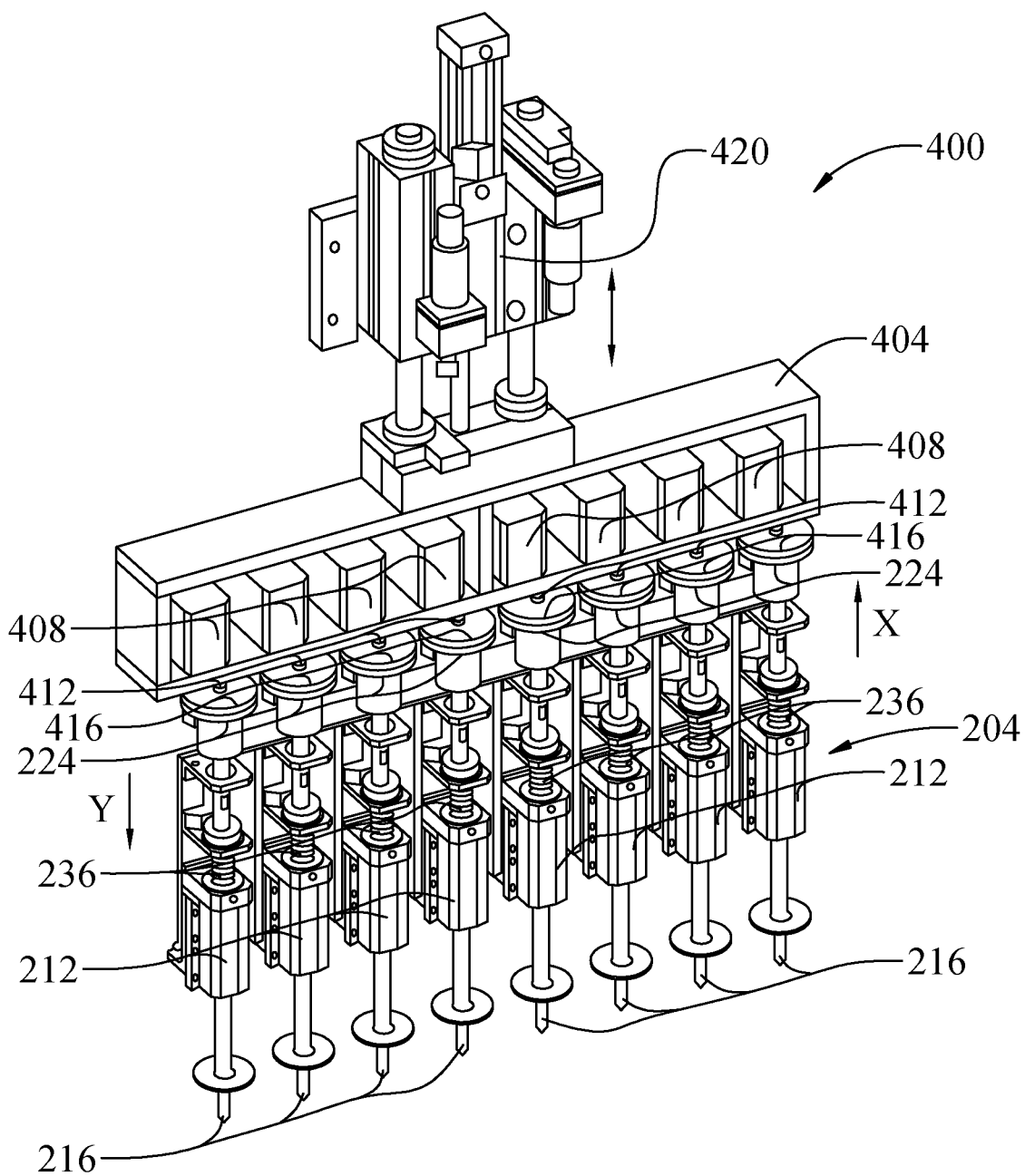
FIG. 6A is an isometric view of a seed orientation station (absent system support structure), of the seed sorter system shown in FIG. 1, in accordance with various embodiments of the present disclosure.
Figure 6B:
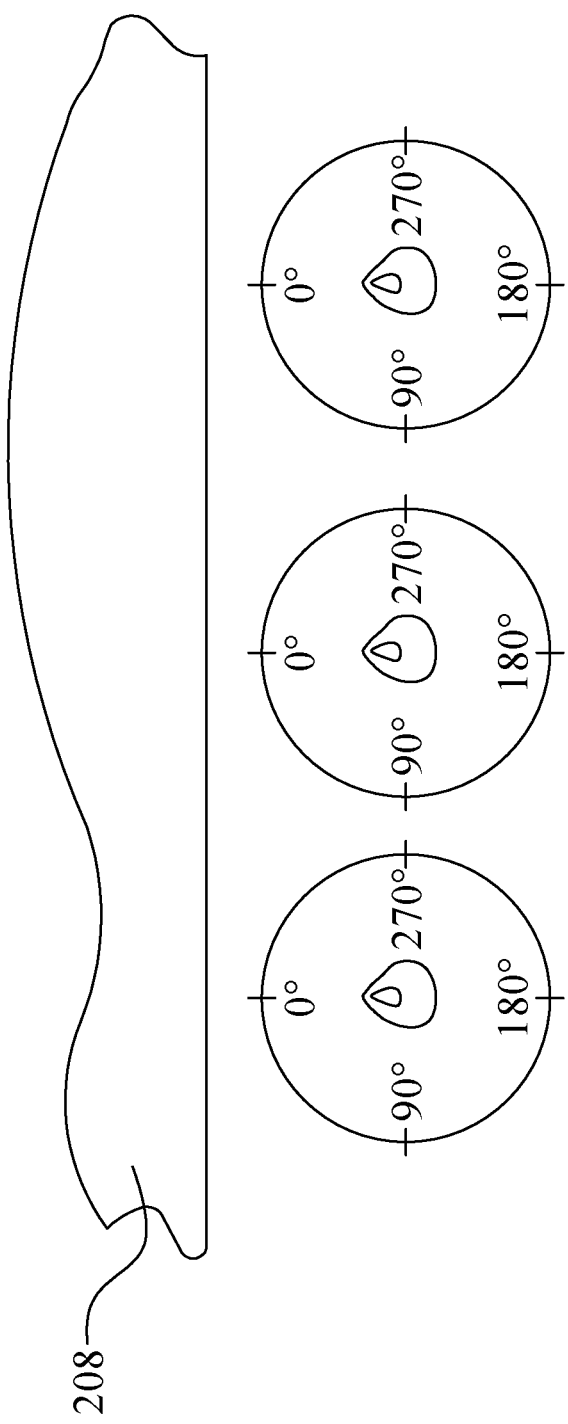
FIG. 6B is an exemplary schematic illustrating a 360° plane in which the seeds are controllably rotated at the seed orientation station, shown in FIG. 6A, such that the seed tips of each seed have a desired orientation.

Referring now to FIGS. 6A and 6B, in various embodiments, the orientation station 400 includes motor bank 404 that includes a plurality of rotary motors 408, e.g., a number of rotary motors 408 equal to the number of RVC 212, independently controlled by the CCS 700. In some embodiments, the rotary motors 408 comprise stepper motors. Each motor 408 includes a rotary shaft 412 having a clutch plate 416 mounted to a distal end thereof. The motor bank 404 is mounted to a linear actuator 420, e.g., a pneumatic slide, that is mounted to system support structure such that when the RVC bank 204 is positioned adjacent the orientation station 400, each motor 408 is positioned directly above a respective one of the RVC devices 212. More specifically, when the RVC bank 204 is positioned adjacent the orientation station 400, the clutch plate 416 of each motor 408 is positioned directly above, and in alignment with, a respective one of the RVC friction plates 224.

Once the imaged set of seeds is advanced to the orientation station 400, the actuator 420 lowers the motor bank 404 such that the clutch plates 416 of each motor 408 engage the corresponding friction plates 224 of the respective RVC device 212. Additionally, the actuator 420 is lowered such that the clutch plates 416 apply force to each friction plate 224 in the Y direction that overcomes the force in the X direction applied by the RVC biasing devices 236. Accordingly, each RVC friction plate 224, rotary shaft 220 and vacuum cup 216 is moved downward, thereby disengaging the RVC locking mechanism and allowing each RVC friction plate 224, rotary shaft 220 and vacuum cup 216 to rotate. Then, based on the analyzed image data collected at the imaging station 300, each motor 408 is independently controlled by the CCS 700 to rotate the respective friction plates 224 and corresponding vacuum cups 216 to independently properly orient each respective seed for sampling at the sample and sort station 500, as described below. More particularly, based on the analyzed image data for each independent seed, each motor 408 is independently controlled to rotate the respective seed such that the tip of the seed is oriented approximately at 0°. More importantly, each seed is independently rotated, if necessary, to position the cap of the seed at approximately 180° such that a sample can be removed from that cap of each seed at the sample and sort station 500, as described below.

Once each seed of the set is oriented with the cap of each respective seed oriented, or positioned, at approximately 180°, the CCS 700 commands the actuator 420 to raise the motor bank 404 to disengage the clutch plates 416 from the friction plates 224. As the motor bank 404 is raised and the clutch plates 416 are disengaged from the friction plates 224, the biasing devices 236 of each RVC device 212 move each respective rotary shaft in the X direction thereby engaging each respective locking device. Thus, each rotary cup 216 and corresponding seed held thereon, is maintained in the orientation with the seed cap at approximately the 180° position, as illustrated in FIG. 6B. The CCS 700 then advances the transfer carousel 208 to position the properly oriented seed set adjacent the sample and sort station 500.

Figure 6C:
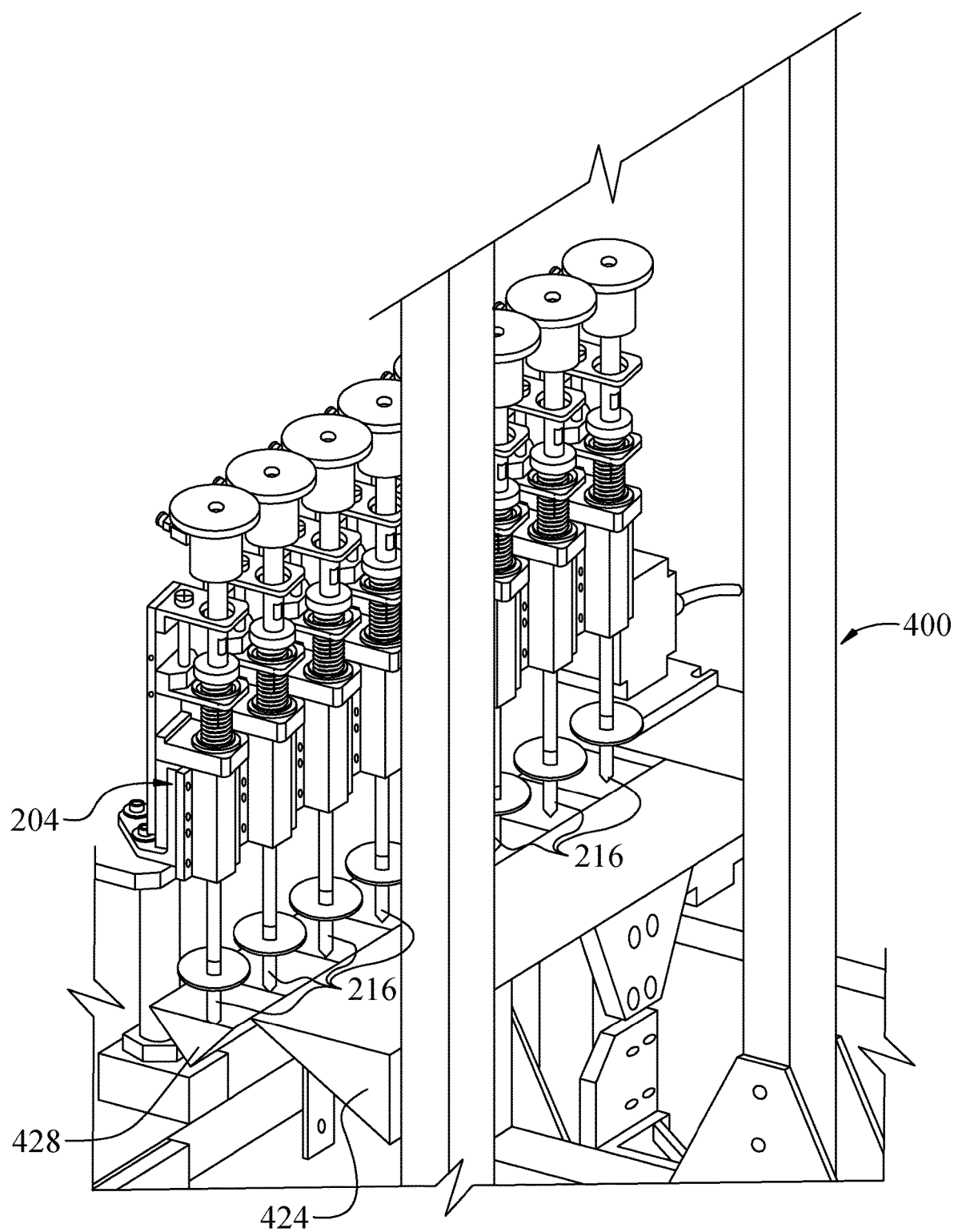
FIG. 6C is an isometric partial view of the seed orientation station shown in FIG. 6A, illustrating a seed purge hopper, in accordance with various embodiments of the present disclosure.

Referring now to FIG. 6C, in various embodiments, the orientation station 400 further includes a seed purge hopper 424 for receiving the set of seeds held by the respective RVC bank 204. The seed purge hopper 424 is mounted to system support structure such that a trough 428 of the seed purge hopper 424 is positioned under the vacuum cups 216 of the respective RVC bank 204 for receiving seeds discharged from the respective vacuum cups 216. More specifically, the seed purge hopper 424 can be utilized to offload all the seeds held by each RVC bank 204 of the seed transport subsystem 200. To offload all the seeds, each RVC bank 204 is sequentially advanced to the orientation station 400 at which time the vacuum source being supplied to each respective vacuum cup 216 is terminated. When the supplied vacuum is terminated, the seeds are released from the vacuum cups 216 and fall into the seed purge hopper trough 428 where they can be collected and returned to the bulk seed hopper 104 at a later time. Thus, if operation of the seed sorting system 10 needs to be terminated, all the seeds held by the RVC banks 204 can be purged and collected.

In various embodiments, the seed sorting system 10 includes an emergency stop button 22, shown in FIG. 1, for stopping and shutting down the seed sorting system 10. For example, in the case of an emergency, the emergency stop button 22 can be depressed and the all operation of the seed sorting system 10 would cease. Also, in various embodiments, the seed sorting system 10 includes a system pause button 26, shown in FIG. 1, for temporarily pausing operation of the seed sorting system 10. For example, if a jam occurred in one of the first transfer tubes 126 of the seed loading station 100 such that one or more RVC banks did not 'pick up' a full set of seeds, the system pause button could be depressed to pause operation of the seed sorting system 10. In the paused state, the vacuum source can remain actuated such that all seeds are retained by the respective RVC vacuum cups 216 until such time as the seeds are purged into the seed purge hopper 424 or operation is reinitiated and the seeds are sampled, as described below.

Figure 7:
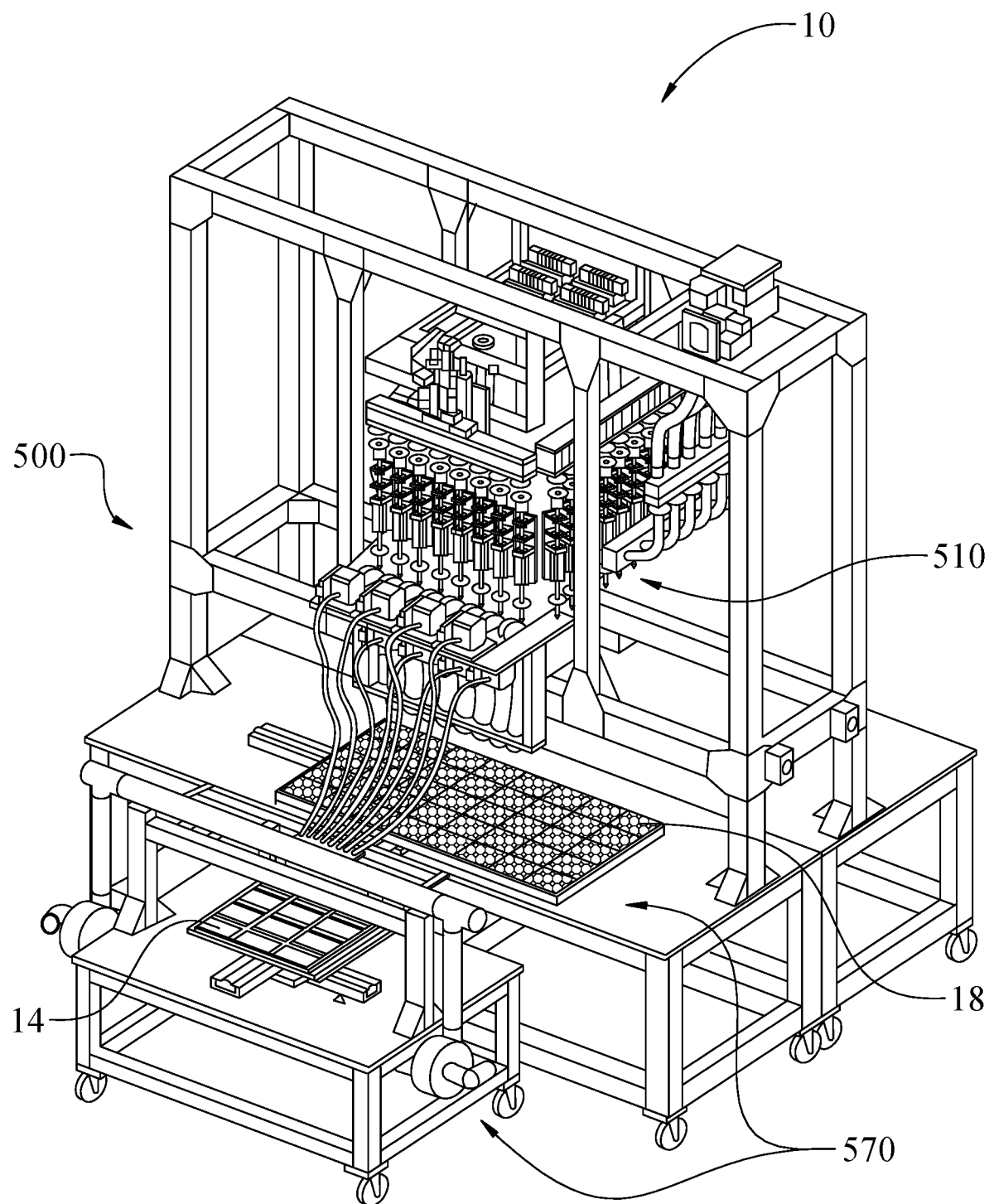
FIG. 7 is an isometric view of the seed sampling system, shown in FIG. 1, illustrating a seed sample and sort station, in accordance with various embodiments of the present disclosure.

Referring now to FIG. 7, in various embodiments, the seed sample and sort station 500 includes a seed sampling subsystem 510 and a seed and sample sorting subsystem 570. The seed sampling subsystem 510 is controllable by the CCS 700 to extract a sample from each seed in the respective seed set positioned adjacent the seed sample and sort station 500. The seed and sample sorting subsystem 570 is additionally controllable by the CCS 700 to sort the sampled seeds to the seed trays 18 and sort the corresponding seed sample to the sample trays 14 while tracking and mapping the locations of the corresponding sampled seeds and seed samples in the respective seed and sample trays 18 and 14. The locations of the seed samples and the locations of the corresponding sampled seeds in the trays 14 and 18 are matched so that the sampled seed may later be correlated to the sample taken therefrom (e.g., after analysis of the sample, etc.).

Referring now to FIGS. 8A, 8B, 8C and 8D, in various embodiments, the seed sampling subsystem 510 includes a plurality of seed grip and chip assemblies 512, e.g., a number of seed grip and chip assemblies 512 equal to the number of RVC devices 212 included in each RVC bank 204. The seed sampling subsystem 510 additionally includes a press plate bank 514 mounted to a linear actuator 516, e.g., a pneumatic slide. The press plate bank 514 includes a plurality of press plates 518 fixedly mounted to a press plate bank header 520 that is coupled to the linear actuator 516. The actuator 516 is mounted to system support structure such that when the RVC bank 204 is positioned adjacent the sample and sort station 500, each press plate 518 is positioned directly above a respective one of the RVC devices 212. More specifically, when the RVC bank 204 is positioned adjacent the orientation station 400, each press plate 518 is positioned directly above, and in alignment with, a respective one of the RVC friction plates 224.

Once the oriented set of seeds is advanced to the sample and sort station 500, the actuator 516 lowers the push plate bank 514 such that the push plates 518 engage the corresponding friction plates 224 of the respective RVC device 212. As the actuator 420 is lowered, the push plates 518 apply force to each friction plate 224 in the Y direction that overcomes the force in the X direction applied by the RVC biasing devices 236. Accordingly, each RVC friction plate 224, rotary shaft 220 and vacuum cup 216 is moved downward, thereby disengaging the RVC locking mechanism. However, since the press plates 518 are fixedly mounted to the header 520, each RVC friction plate 224, rotary shaft 220 and vacuum cup 216 can not rotate and each seed remains properly oriented as it is moved downward in the Y direction.

Figure 8A:
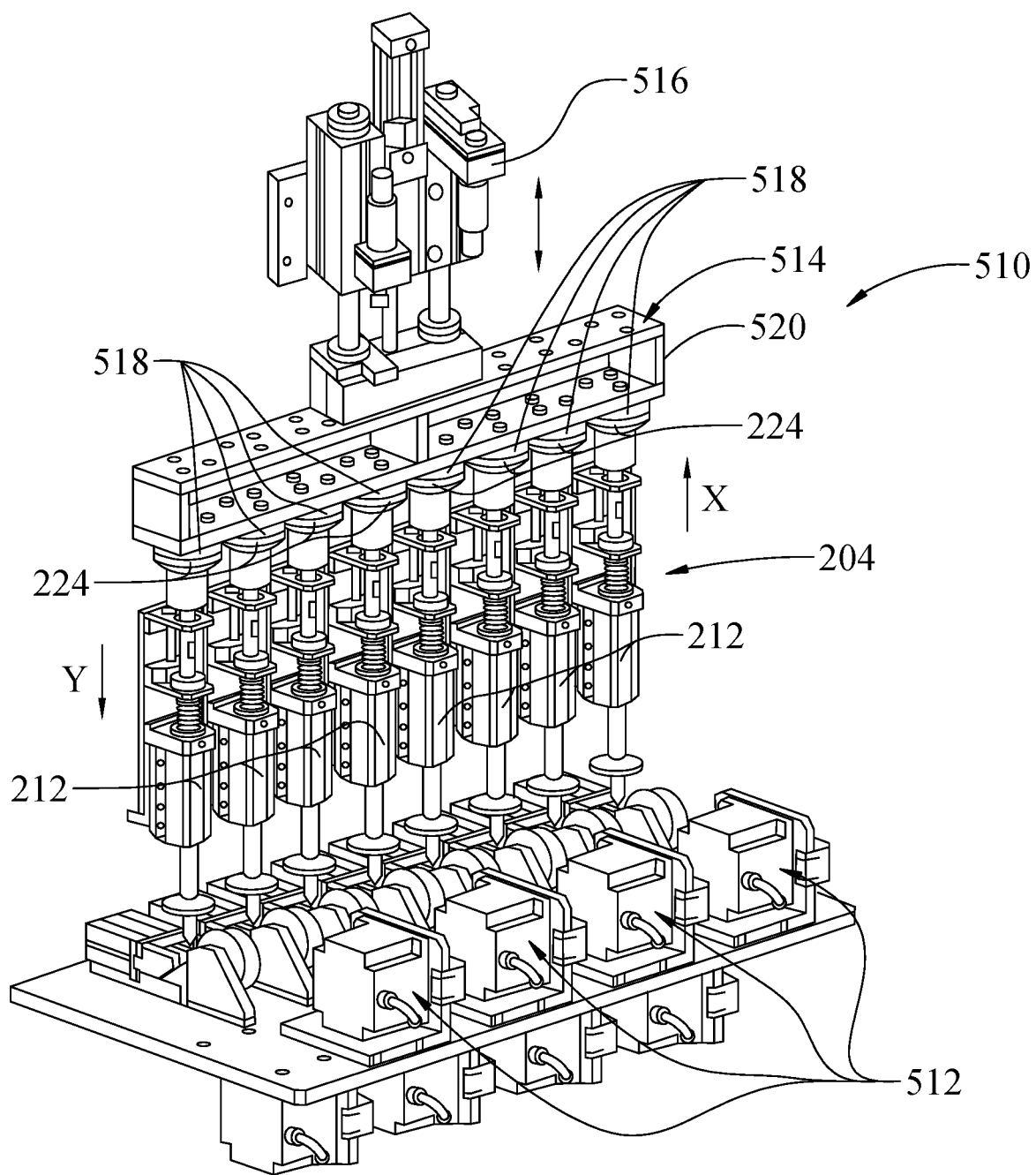
FIG. 8A is an isometric view of a seed sampling subsystem (absent system support structure), of the seed sample and sort station, shown in FIG. 7, in accordance with various embodiments of the present disclosure.
Figure 8B:
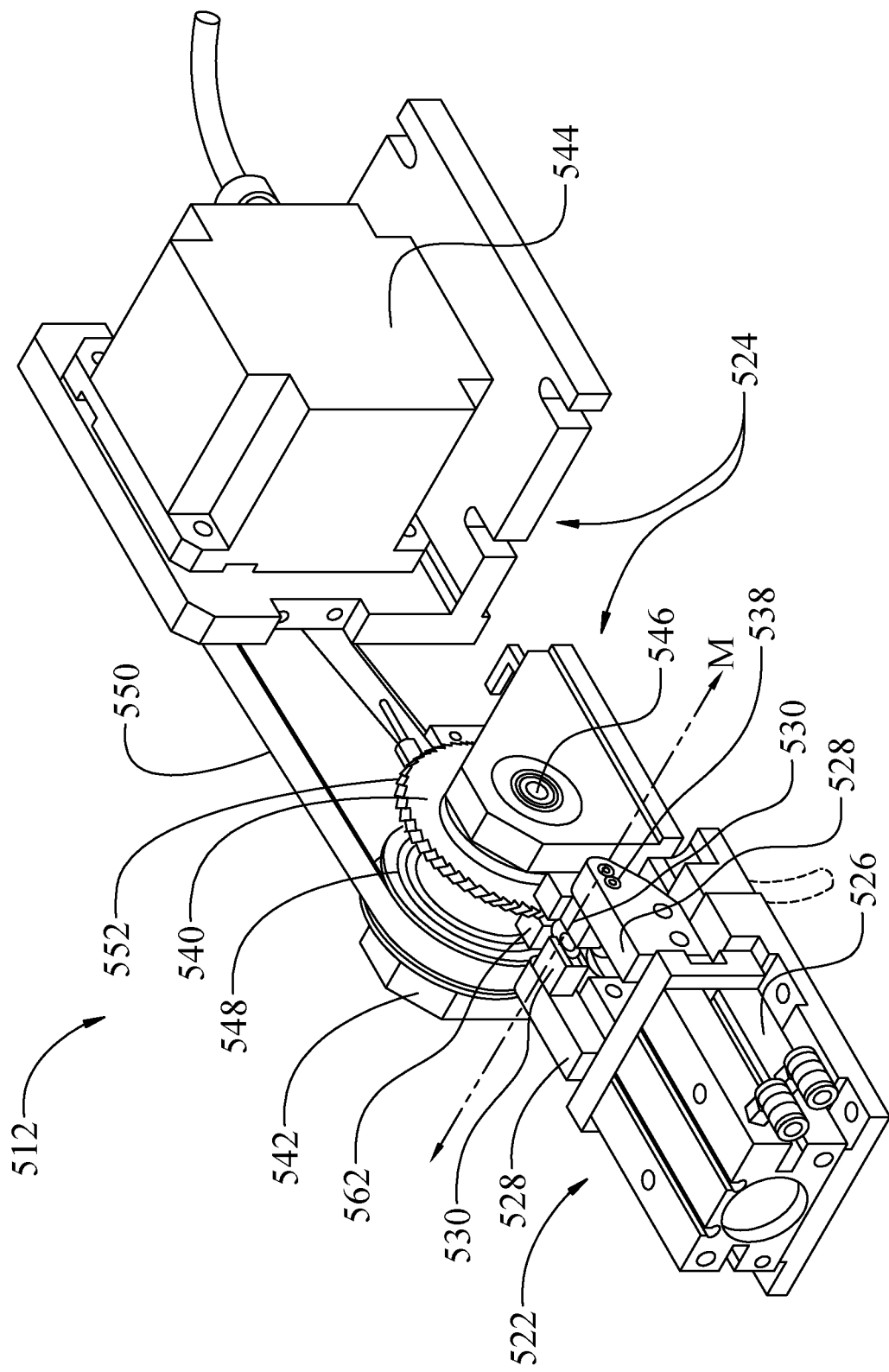
FIG. 8B is an isometric view of the seed grip and chip assembly of the seed sampling subsystem, shown in FIG. 8A, in accordance with various embodiments of the present disclosure.
Figure 8C:
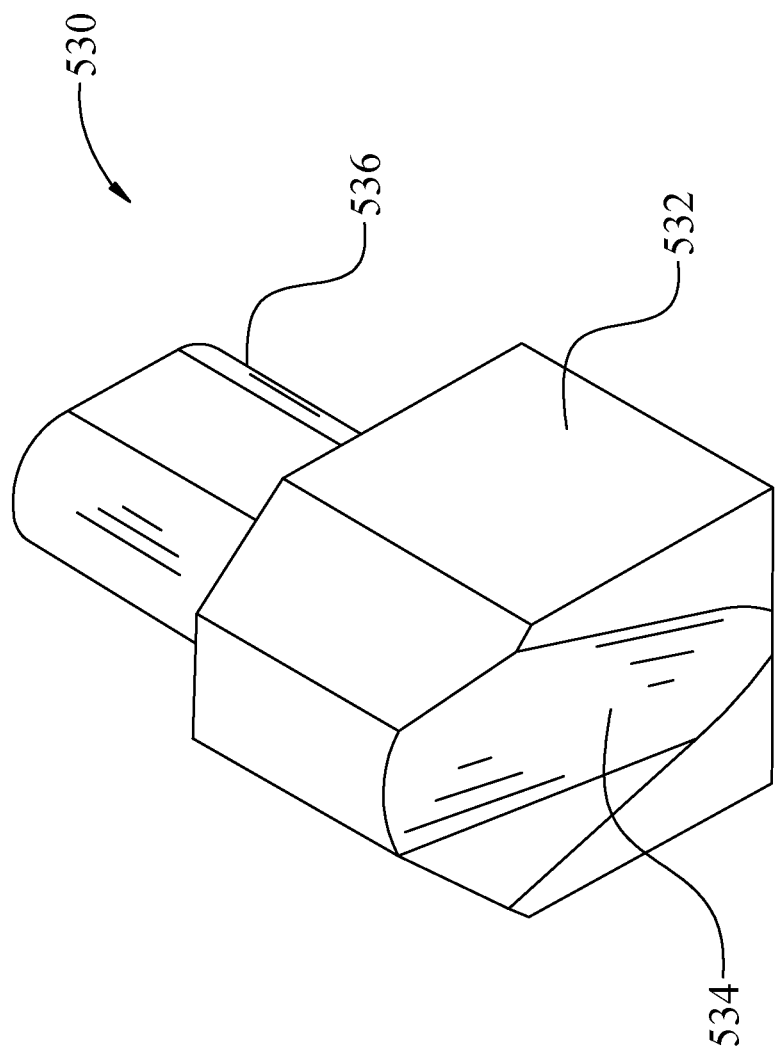
FIG. 8C is an isometric view of an exemplary seed gripping finger included in the seed grip and chip assembly, shown in FIG. 8B, in accordance with various embodiments of the present disclosure.
Figure 8D:
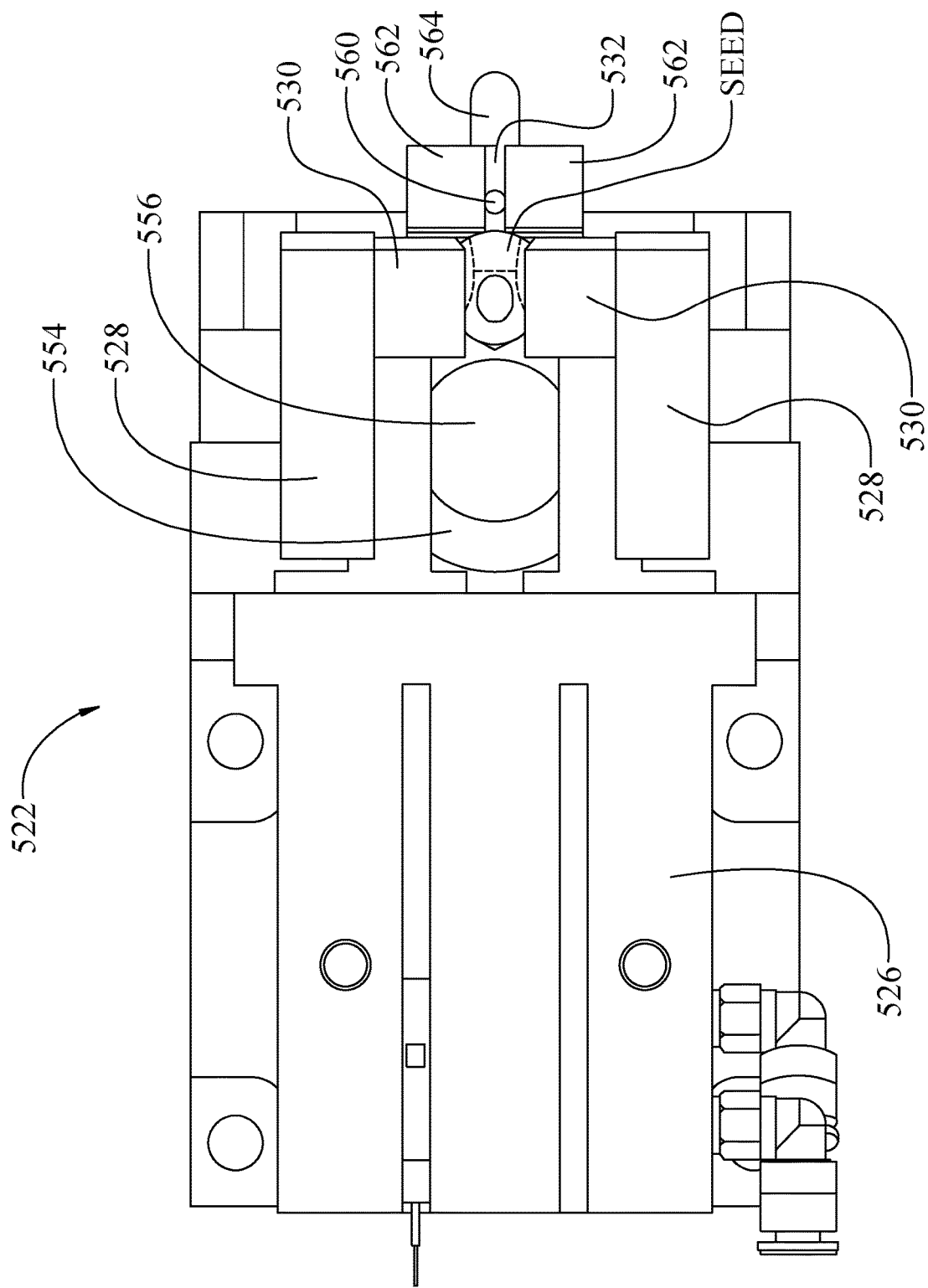
FIG. 8D is a top view of a seed gripping mechanism of the seed grip and chip assembly, shown in FIG. 8B, in accordance with various embodiments of the present disclosure.

With particular reference to FIGS. 8B and 8D, in accordance with various embodiments, each grip and chip assembly 512 includes a seed gripping mechanism 522 and a sample extraction mechanism 524. Although, each grip and chip assembly 512 is independently controlled by the CCS 700, the structure and function for each grip and chip assembly 512 is substantially identical. Therefore, the structure and function of the plurality of grip and chip assemblies will be described herein with reference to a single grip and chip assembly 512. The seed gripping mechanism 522 is operable, as controlled by the CCS 700, to firmly hold each respective seed as the sample extraction mechanism 524 removes a portion, i.e., a sample, of the seed coat and inner seed material from the crown of the respective seed. The extracted sample can then be utilized to test and analyze the various traits of the respective seed. Importantly, the sample is extracted from the crown in a non-destructive manner such that germination viability of the seeds can be preserved.

In various embodiments, the seed gripping mechanism 522 includes an actuator 526, e.g., a pneumatic clamp, that is controllable by the CCS 660 to bidirectionally move a pair of opposing actuator arms 528 toward and away from each other, i.e., open and close the actuator arms 528. For example, in various embodiments, the actuator 526 is operable to move the opposing actuator arms 528 toward and away from each other along the line M (FIG. 8B). The actuator arms 528 are structured to removably retain a pair of opposing seed gripping fingers 530 structured to firmly hold the respective seed as the sample is extracted by the sample extraction mechanism 524, as described below. An exemplary gripping finger 530 is illustrated in FIG. 8C. Each gripping finger 530 includes a head 532 having a contoured face 534. The face 534 can be shaped or formed to have any conformation suitable for firmly and steadily holding the respective seed as the sample is extracted. In various embodiments, the face 534 is particularly designed to have a wedge-like conformation such that as the actuator 526 closes gripping fingers 530 around the seed, the seed is forced toward a cutting wheel 540 of the sample extraction mechanism 524 and into abutment with a justification block 562 of the sample extraction mechanism 524. The justification block 562 includes a cutting wheel guide slot 533 that allows the cutting wheel 540 access to seed. Thus, the gripping fingers 530 firmly and justification block 562 hold the seed on three sides and prevent the respective seed from moving in a direction away from the sample extraction mechanism 524 as the sample is being extracted. In various embodiments, the gripping finger head 532 is connected to, or integrally formed with, a mounting post 536 structured to fit within, or mate with, a mounting hole 538 in each actuator arm 528.

When the RVC bank 204 and properly oriented seed set are advanced to the seed sample and sort station 500, the CCS 700 commands the seed gripping actuator 526 to open the actuator arms 528 such that the gripping finger faces 534 have a space between them large enough to allow a seed to be easily positioned therebetween. The CCS 700 then commands the press plate bank actuator 516 to lower the press plate bank 514 to engage the press plates 518 with the friction plates 224. More particularly, the force on the friction plates 224 moves the vacuum cups 216 and respective seed downward toward a sampling position, i.e., the gap between gripping fingers 530. Each grip and chip system 512 is mounted to system support structure such that each sampling position, or gap, between the gripping finger faces 534 is precisely aligned below the respective vacuum cup tip 232. Thus, when the press plate bank actuator 516 pushes the friction plates 224, vacuum cups 216 and oriented seeds downward, the oriented seeds are moved to the sampling positions between the gripping fingers 530 of the respective seed gripping mechanism 522.

The CCS 700 then commands the seed gripping actuator 526 to close the actuator arms 528 such that the gripping finger faces 534 engage the respective seed to firmly retain the seed without damaging the seed. Once the seed is firmly retained between the gripping fingers 530, the push plate bank actuator can be commanded to raise, and the vacuum provided at the vacuum cup tip 232 terminated, to thereby release the respective seed. Or, alternatively, the CCS 700 can maintain the vacuum cup 216 in contact with the seed to provide additionally support for the seed as the sample is being extracted.

The sample extraction mechanism 524 includes cutting wheel 540 rotationally mounted within a cutting wheel fixture 542 and rotationally driven by a cutting wheel motor 544. Although the cutting wheel 540 is shown in FIG. 8B to be belt driven by the cutting wheel motor 544, alternatively the cutting wheel 540 can be shaft driven, chain driven, direct gear driven, etc., by the cutting wheel motor 544 and remain within the scope of the present disclosure. The cutting wheel 540 is mounted on a shaft 546 that is rotationally mounted within the cutting wheel fixture 542. Additionally, a drive wheel 548 is mounted to, or formed with, the shaft and operatively coupled to the cutting wheel motor 544, for example, by a drive belt 550, such that actuation of the motor 544 will rotate the drive wheel 548, shaft 546 and cutting wheel 540 within the cutting wheel fixture 542. More specifically, the cutting wheel 540 is mounted to the shaft 546 in a cam fashion, e.g., the shaft 546 can be an offset shaft, such that as the drive wheel 548 and shaft 546 are rotated by the motor 544, a peripheral cutting edge 552 of the cutting wheel 540 rotates and progressively moves toward the seed gripping mechanism 552, and specifically toward the seed retained between the gripping fingers 530. The cutting edge 552 comprises an abrasive or sharp-edged surface, e.g., a saw-toothed surface, that will remove the seed coat and inner seed material from the crown of the respective seed. Thus, as the cutting wheel 540 is rotated, the cutting edge 552 will contact and begin to cut or abrade the seed crown. As the cutting wheel 540 continues to rotate, the cutting edge 552 will penetrate a desired depth or distance into the crown, depending on the amount of angular rotation of the cutting wheel 540, as controlled by the CCS 700. That is, the greater the amount of angular rotation of the cutting the wheel 540, the deeper the cutting edge 552 will penetrate into the seed crown and the more sample that will be extracted.

Figure 9A:
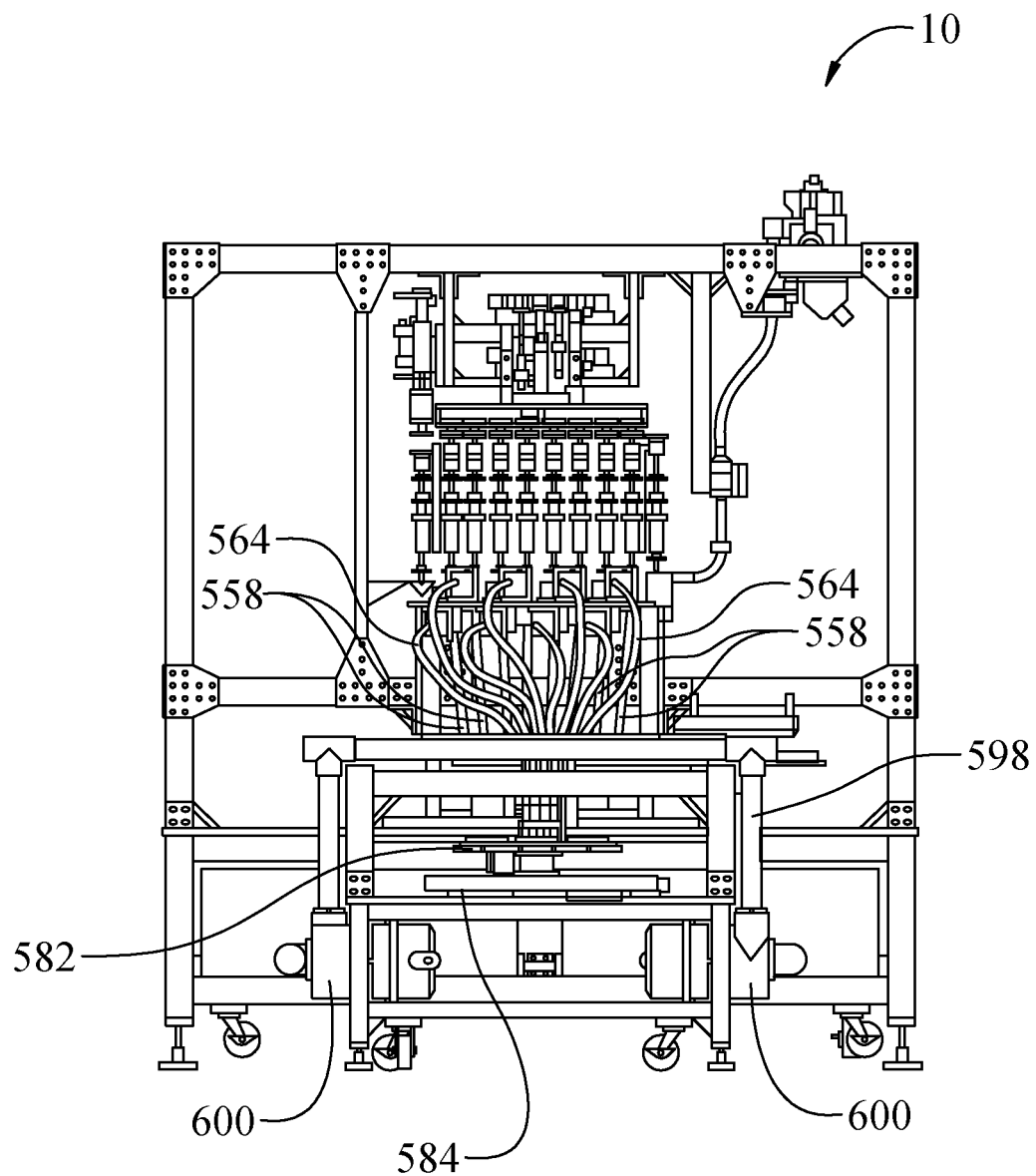
FIG. 9A is a front view of a seed and sample sorting subsystem, of the seed sample and sort station, shown in FIG. 7, in accordance with various embodiments of the present disclosure.
Figure 9B:
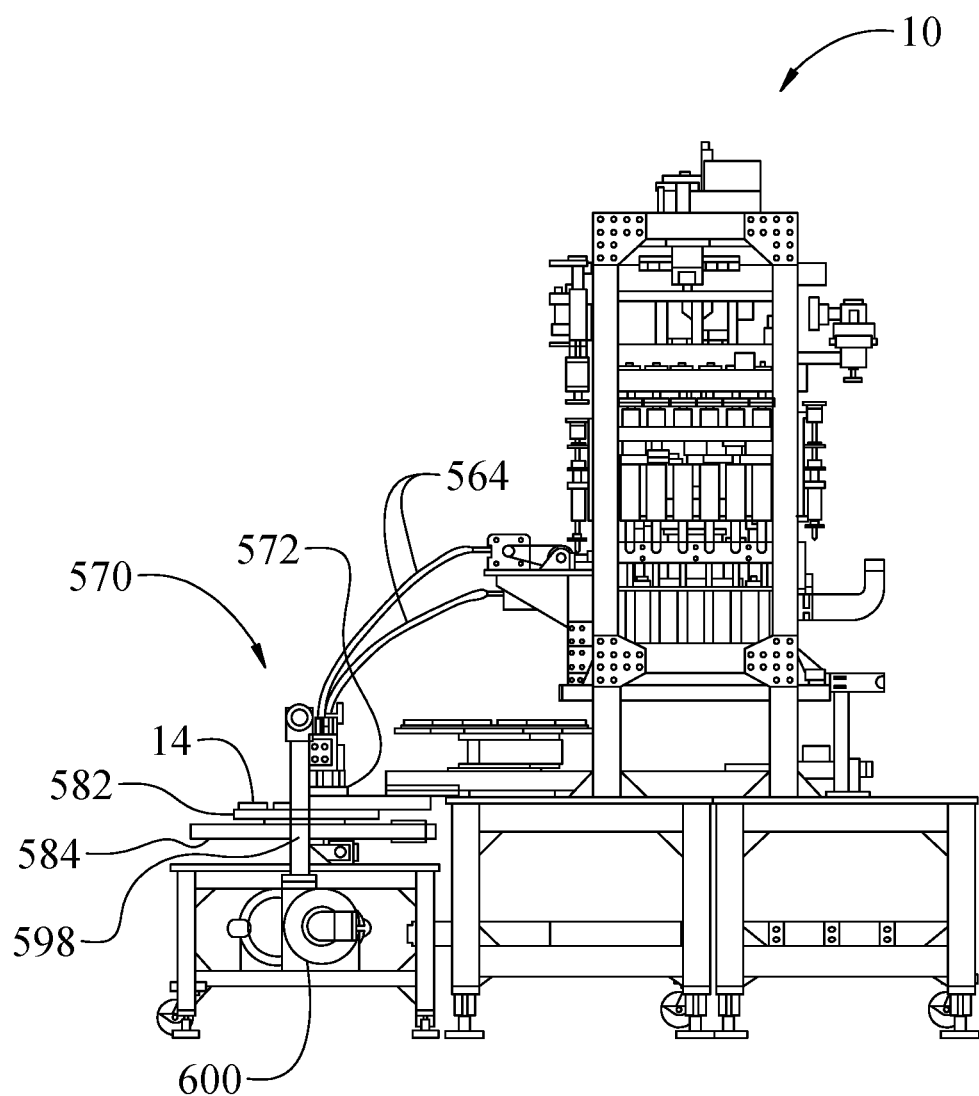
FIG. 9B is a side view of seed and sample sorting subsystem shown in FIG. 9A.
Figure 9C:
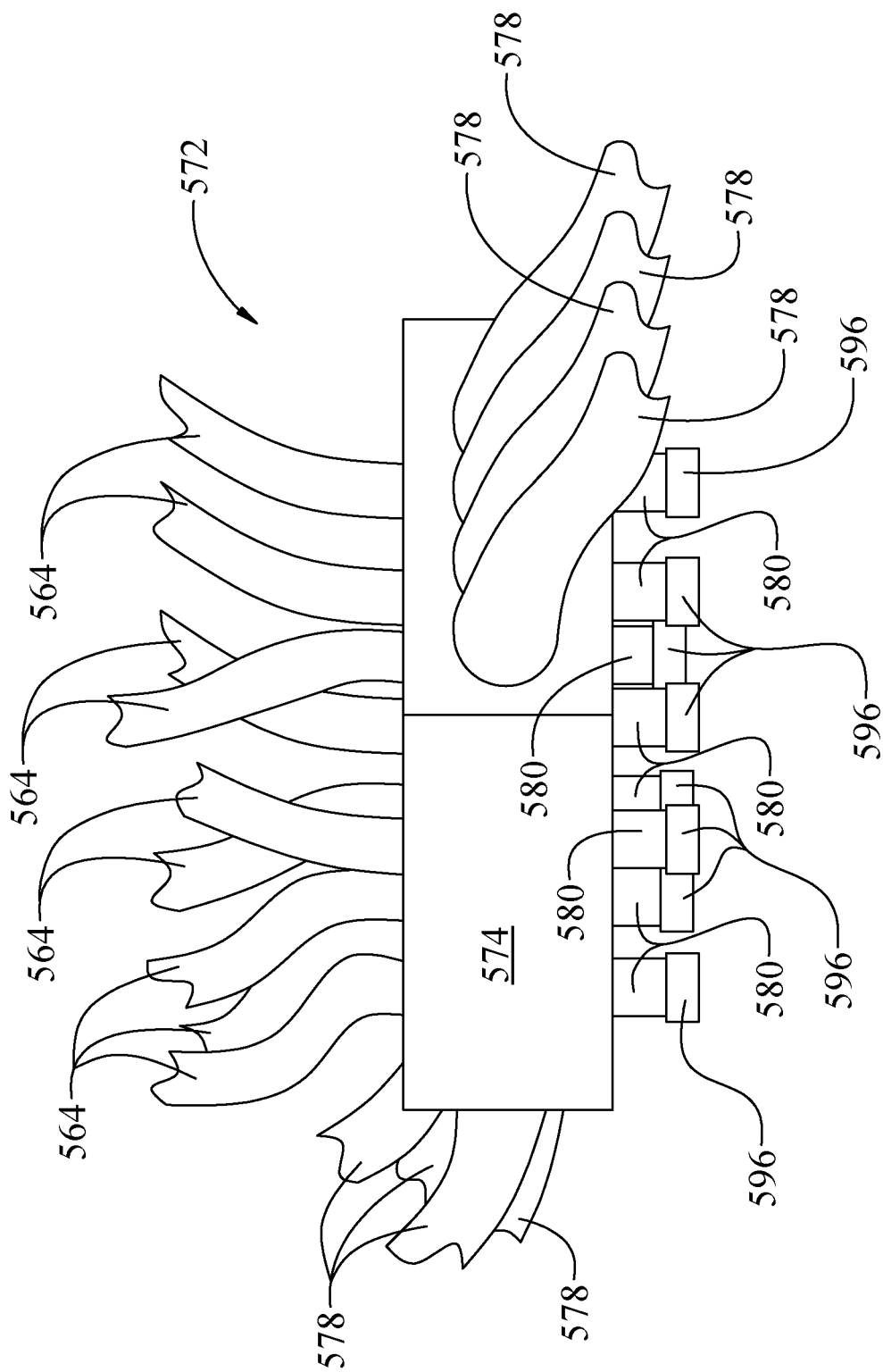
FIG. 9C is diagonal view of a sample extraction nozzle manifold of the seed and sample sorting subsystem shown in FIGS. 9A and 9B, in accordance with various embodiments of the present disclosure.

The seed gripping mechanism 522 additionally includes a seed dump bowl 554 (FIG. 8D) having a drain port 556 formed in the bottom of the dump bowl 554. The dump bowl 554 is shaped to funnel a sampled seed into the drain port 556 after a sample has been removed from the respective seed and the seed is released from being held between the gripper fingers 530. A drain tube 558 (shown in FIGS. 9A and 9B) is connected to the drain port 556 to transfer the released seed to one of the seed trays 18 positioned below the grip and chip assembly 512, as describe below. The seed gripping mechanism 522 further includes a sample extraction orifice 560 located in the justification block 562, below the cutting wheel guide 533, such that cutting edge 552 and periphery portion of the cutting wheel 540 extends over the sample extraction orifice 560. A sample extraction tube 564 (FIGS. 9A and 9B) is connected to the sample extraction orifice 560 and a vacuum is controllably provided to the sample extraction tube 564 and thus, at the sample extraction orifice 560. As the cutting wheel 540 removes the sample from the respective seed, the vacuum provided at the sample extraction orifice 560, via the sample extraction tube 564, draws the sample into the sample extraction orifice 560. The sample is then passed through the sample extraction tube 564 and deposited into one of the sample trays 14.

Therefore, once the seed is retained between the gripping fingers 530, the CCS 700 commands the cutting wheel motor 544 to angularly rotate the drive wheel 548 through a predetermined angle and at a predetermined rate of rotation. For example, the CCS 700 can command the cutting wheel motor 554 to rotate the drive wheel 548 ninety-five degrees at thirty revolutions-per-minute (RPMs). Accordingly, the cutting wheel 540 is rotated through the predetermined angle, at the predetermined RPMs. As the cutting wheel 540 rotates, the cam action of cutting wheel 540 mounting rotates and advances the cutting edge 552 toward and into the seed, thereby removing a sample from the respective seed. As the sample is removed, the vacuum at the sample extraction orifice 560 draws the sample into the sample extraction tube 564 where the sample is transferred to one of the sample trays 14. The CCS 700 then commands the cutting wheel motor 544 to reverse the direction of rotation to withdraw the cutting wheel 540 from the seed and return the cutting wheel to a home position, ready to remove a sample from a subsequent seed. Subsequent to, or substantially simultaneously with the withdrawal of the cutting wheel 540, the CCS 700 commands the seed gripping mechanism 522 to release the sampled seed, allowing the seed to fall, via gravity, vacuum or forced air, into the drain tube 556 to transfer the sampled seed to one of seed trays 18.

Figure 8E:
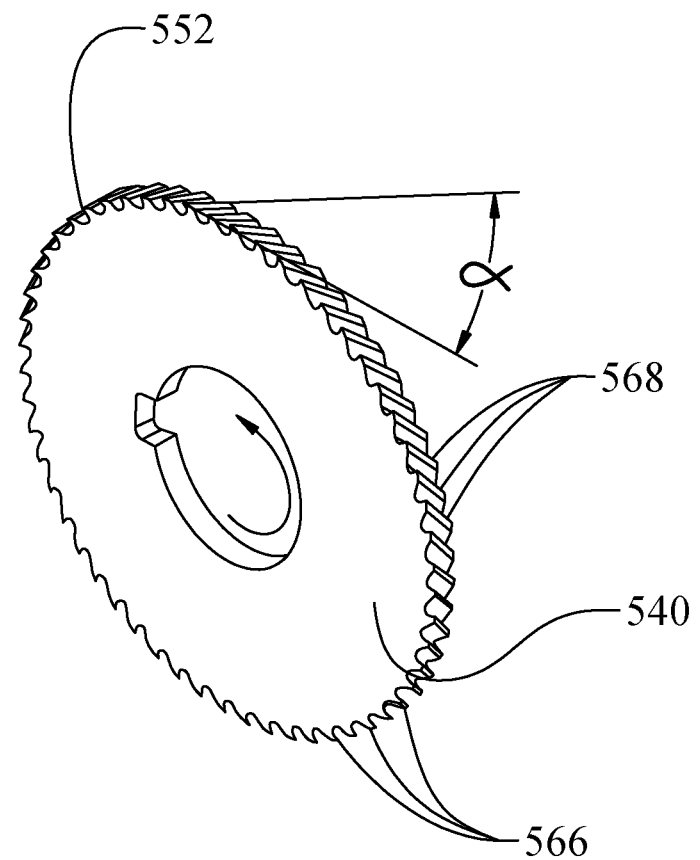
FIG. 8E is an isometric view of an exemplary cutting wheel of the seed grip and chip assembly, shown in FIG. 8B, in accordance with various embodiments of the present disclosure.

Referring now to FIG. 8E, in various embodiments, the cutting wheel 540 is structured to have a saw-toothed cutting edge 552 that includes a plurality of teeth 566. Moreover, each tooth 566 includes a lateral cutting tip 568 that is formed to avoid movement, e.g., 'chattering', of the seed being sampled and allow the seed to remain stationary within the gripping fingers 530. For example, the lateral cutting tip 568 of each tooth can have a specific angle α, e.g., a 60° angle, such that as the cutting wheel 540 cuts through the respective seed, a leading end of the cutting tip 568 of each subsequent tooth 566 engages the seed before a trailing end of the cutting tip 568 of each preceding tooth 566 disengages the seed.

In various embodiments, each cutting wheel 540, i.e., each cutting wheel motor 544, is independently controlled by the CCS 700, but each cutting wheel 540 is commanded to have approximately the same rotational speed and/or angular rotation. Therefore, when a set of seeds is held within the seed gripping mechanisms 522, the respective cutting wheels 540 are each commanded to rotate through approximately the same angle of rotation and at the same speed. Accordingly, the cam rotation of the cutting wheels 540, as described above, will advance the respective cutting wheels 540 approximately the same distance toward each of the seed. Thus, smaller seeds may not have the same amount of sample extracted as larger seeds. In such embodiments, the rotational speed and/or amount of angular rotation for each cutting wheel 540 is determined by empirical data and programmed into the CCS 700.

In various other embodiments, each cutting wheel 540, i.e., each cutting wheel motor 544, is independently controlled by the CCS 700. Therefore, the rotational speed and/or amount of angular rotation for each independent cutting wheel 540 can be controlled and adjusted for each seed positioned and held by the seed gripping mechanism 522 of each respective grip and chip assembly 512. For example, the seed held within a seed gripping mechanism 522 of a first grip and chip assembly 512 may be smaller in size than a seed held within a seed gripping mechanism 522 of an adjacent second grip and chip assembly 512. In such a case, the cutting wheel 540 of first grip and chip assembly 512 can be commanded to have a greater angular rotation than the cutting wheel 540 of second grip and chip assembly 512. Therefore, the cam rotation of the cutting wheels 540, as described above, will advance the cutting wheel 540 of the first chip and grip assembly 512 further toward the smaller seed such that approximately equal amounts of sample will be extracted from the smaller seed as from the larger seed. Furthermore, in such embodiments, the rotational speed and/or amount of angular rotation for each independent cutting wheel is based on the imaging data collected for each respective seed at the imaging station 300.

Referring now to FIGS. 9A, 9B, 9C, 9D and 9E, as described above, as the sample is extracted from the respective seed, the sample is drawn into the sample extraction tube 564. More specifically, the sample extraction orifice 560 of each grip and chip assembly 512 has a first end of a respective sample extraction tube 564 connected thereto, and a second end of each respective sample extraction tube 564 is connected to a sample extraction nozzle (SEN) manifold 572. The SEN manifold 572 includes a manifold block 574 to which the sample extraction tubes 564 are connected, and from which a plurality of exhaust tubes 578 extend, e.g., a number of exhaust tubes 578 equal to the number of sample extraction tubes 564 can extend from the manifold block 574. The SEN manifold 572 additionally includes a plurality of discharge nozzles 580 that are in fluid communication with the extraction tubes 564. More specifically, the manifold block 574 includes a number of bores or passages (not shown), equal to the number of sample extraction tubes 564, which extend through the manifold block 574. Each extraction tube 564 is connected to a first end of a corresponding manifold block bore and a corresponding one of the discharge nozzles 580 extends from an opposing second end of each manifold block bore.

Figure 9D:
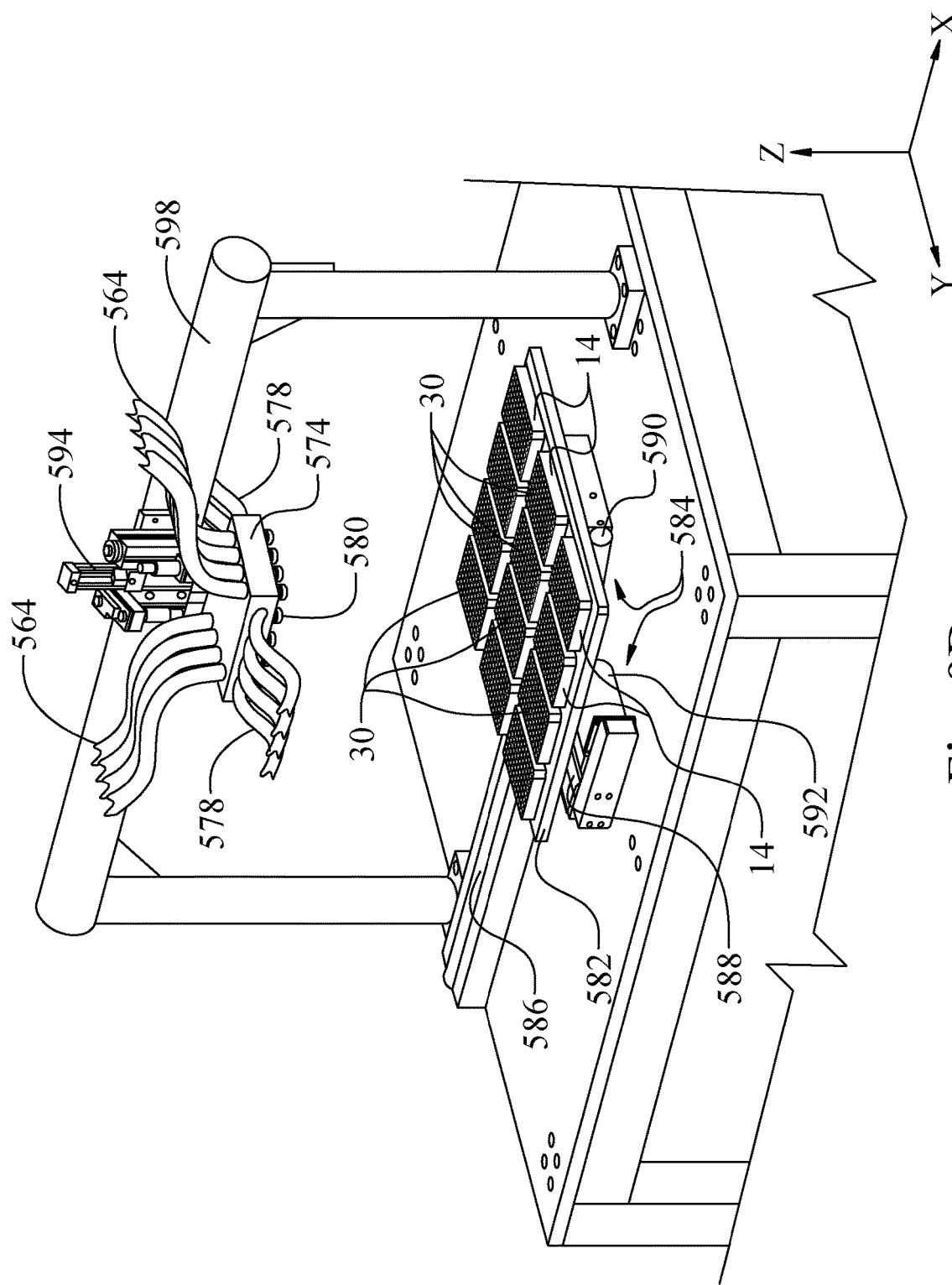
FIG. 9D is an isometric view of a sample tray platform and X-Y translation stage included in the seed and sample sorting subsystem shown in FIGS. 9A and 9B.

As most clearly illustrated in FIG. 9D, the seed and sample sorting subsystem 570 further includes a sample tray platform 582 adapted to securely retain a plurality of the sample trays 14 in fixed positions and orientations. Each sample tray 14 includes a plurality of sample wells 30, each of which are adapted for receiving a sample extracted by one of the grip and chip assemblies 512. For example, in various embodiments, each sample tray 14 can be a ninety-six well tray. Moreover, the discharge nozzles 580 extending from the SEN manifold 572 are spaced apart and arranged to be congruent with the spacing and arrangement of the wells 30 within the sample trays 14. The sample tray platform 582 is mounted to an X-Y stage 584 that is a two-dimensional translation mechanism, including a X axis translating track 586 and a Y axis translating track 588. The X-Y stage 584 additionally includes a first linear actuator 590 operable to bidirectionally move a first carriage (not shown) along the length of the X axis translating track 586. The X-Y stage 584 further includes a second linear actuator 592 operable to bidirectionally move a second carriage (not shown) along the length of the Y axis translating track 588. The Y axis translating track 588 is mounted to the first carriage and the sample tray platform 582 is mounted to the second carriage.

The SEN manifold 572 is connected to system support structure to position the SEN manifold 572 above the X-Y stage 584 and the sample platform 582 holding the plurality of sample trays 14. More particularly, the SEN manifold 572 is mounted to a linear actuator 594, e.g., a pneumatic slide, controllable by the CCS 700 to bidirectionally move the SEN manifold 572 along the Z axis, e.g., up and down. The first and second linear actuators 590 and 592 are controlled by the CCS 700 to precisely move the sample tray platform 582 in two dimensions. More particularly, the first and second actuators 590 and 592 move the sample tray platform 582 within an X-Y coordinate system to precisely position any selected group of adjacent wells 30 of any one or more selected sample trays 14 at a target location directly beneath the SEN manifold 572.

In operation, prior to the grip and chip assemblies 512 extracting samples from the respective seeds advanced to the seed sample and sort station 500, the CCS 700 controls the X-Y stage 584 to position a selected group of wells 30 at the target location. The CCS 700 then commands the SEN manifold actuator 594 to lower the SEN manifold 572 to position each of the discharge nozzles 580 in alignment with and in close proximity to, or in contact with, a corresponding one of the wells 30. Once the selected group of wells 30 is positioned at the target location and the SEN manifold 572 is lowered, the CCS 700 commands the grip and chip assemblies 512 to extract the samples from the respective seeds. Each sample is drawn into a corresponding sample extraction tube 564, as described above, and the vacuum provided to each sample extraction tube 564 transfers each sample through the respective sample extraction tube 564 to the corresponding discharge nozzle 580. Each seed is then discharged into the corresponding sample tray wells 30. The SEN manifold actuator 594 then raises the SEN manifold 572, a subsequent group of wells 30 is positioned at the target position, and the SEN manifold 572 is lowered in preparation for a subsequent set of samples to be extracted and deposited into the wells 30.

In various embodiments, each discharge nozzle 580 includes a seal 596 that contacts the sample tray(s) 14 and creates a seal between each discharge nozzle 580 and the corresponding well 30 when the SEN manifold 572 is lowered. Thus, the seals 596 ensure that substantially all the sample being discharged from each discharge nozzle 580 is deposited into the corresponding well 30 without cross-contamination by adjacent samples escaping around the discharge nozzles 580. The seals 596 can be any seal suitable for creating a seal between each discharge nozzle 580 and the corresponding well 30, e.g., an O-ring, gasket or bushing.

As the sample trays 14 are placed on the sample tray platform 582, a tray identification number, e.g., a bar code, for each sample tray 14 and the location of each sample tray 14 on the platform 582 is recorded. Additionally, as each extracted sample is deposited into a well 30, an X-Y location of the well 30 on the sample tray platform 582 is recorded. The recorded tray and well positions on the sample tray platform 582 can then be compared to the X-Y locations of each deposited extracted sample, to map the specific extracted sample in each well 30 of each sample tray 14. In various embodiments, the sample tray platform 582 is removably coupled to the X-Y stage 584 such that one or more sample tray platforms 582 can be loaded with the sample trays 14 offline, i.e., away from the seed sorter system 10, and conveniently coupled to and decoupled from the X-Y stage 584.

Additionally, in various embodiments, the extraction tubes 564 are fabricated from static dissipative tubing so that a portion of the extracted samples do not stick to the inside walls of the extraction tubes 564 and cause cross-contamination of the samples. Furthermore, in various embodiments, the seed and sample sorting subsystem is structured and operable to 'blow out' the extraction tubes 564 and discharge nozzles 580 between cycles. Therefore, any sample residue accumulated in the extraction tubes 564 and discharge nozzles 580 is cleaned out between cycles. For example, air pressure can be drawn or forced through the extraction tubes 564 and discharge nozzles 580 and exhausted into the exhaust tubes 578. The exhaust tubes 578 can be coupled to an exhaust manifold 598 that carries any residual sample particles to collection chambers 600, where the particles are filtered out of the exhausted air, i.e., separated from the exhausted air.

Figure 9E:
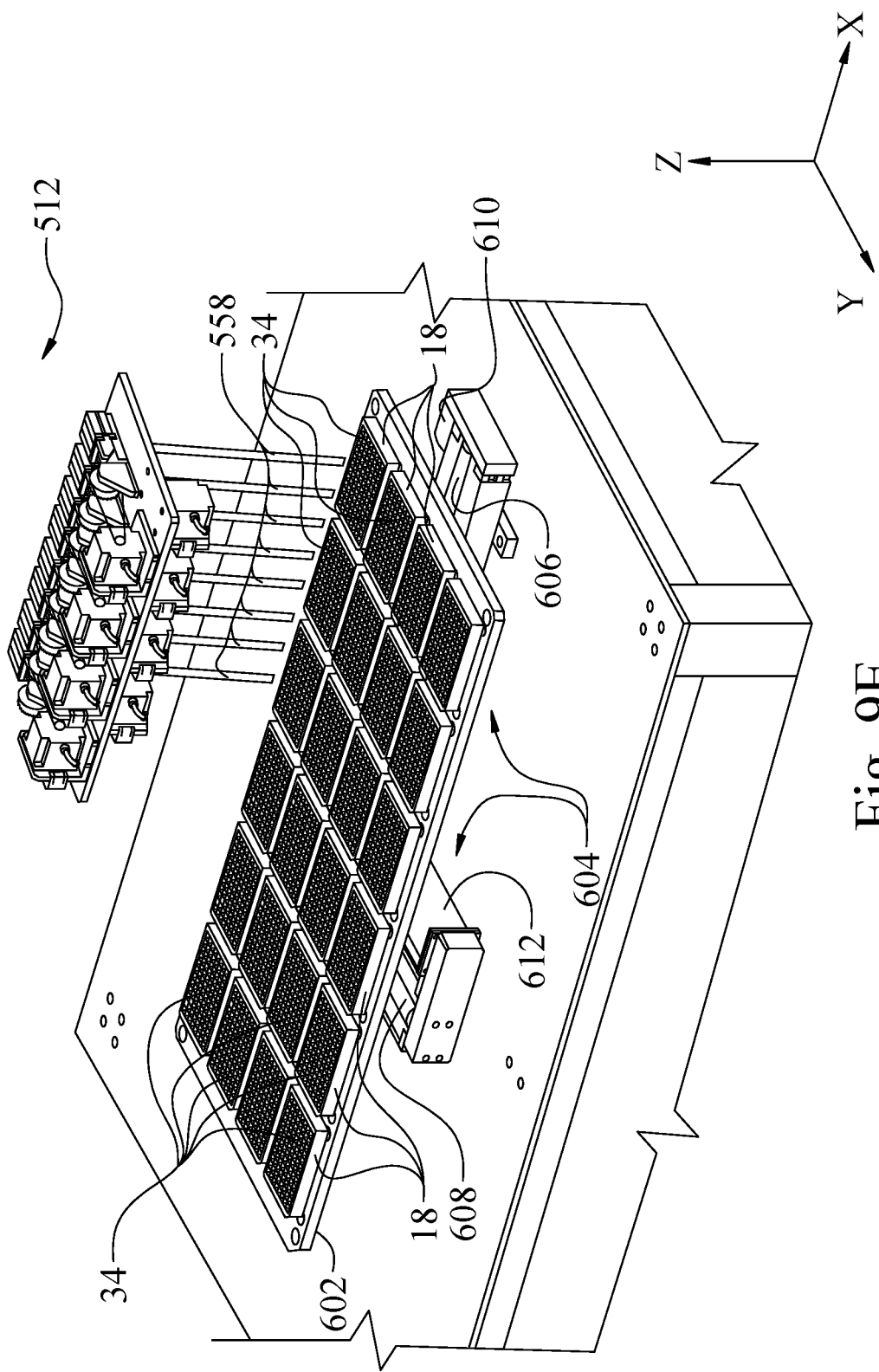
FIG. 9E is an isometric view of a seed tray platform and X-Y translation stage included in the seed and sample sorting subsystem shown in FIGS. 9A and 9B.

As most clearly illustrated in FIG. 9E, the seed and sample sorting subsystem 570 still further includes a seed tray platform 602 adapted to securely retain a plurality of the seed trays 18 in fixed positions and orientations. Each seed tray 18 includes a plurality of seed wells 34, each of which are adapted for receiving a seed after the respective seed has been sampled by one of the grip and chip assemblies 512. For example, in various embodiments, each seed tray 18 can be a twenty-four well tray. The bank of grip and chip assemblies 512 is mounted to system support structure above the seed tray platform 602 such that seeds can be dispensed through the drain tubes 558 into selected seed wells 30 of selected seed trays 18.

The seed tray platform 602 is mounted to an X-Y stage 604. The X-Y stage 604 is a two-dimensional translation mechanism, including an X axis translating track 606 and a Y axis translating track 608. The X-Y stage 604 additionally includes a first linear actuator 610 operable to bidirectionally move a first carriage (not shown) along the length of the X axis translating track 606. The X-Y stage 604 further includes a second linear actuator 612 operable to bidirectionally move a second carriage (not shown) along the length of the Y axis translating track 608. The Y axis translating track 608 is mounted to the first carriage and the seed tray platform 602 is mounted to the second carriage.

The first and second linear actuators 610 and 612 are controlled by the CCS 700 to precisely move the seed tray platform 602 in two dimensions. More particularly, the first and second actuators 610 and 612 move the seed tray platform 602 within an X-Y coordinate system to precisely position any selected well 34 of any selected seed tray 18 at a target location beneath a selected one or more of the drain tubes 558. In various embodiments, the drain tubes 558 are held in linear alignment by system support structure and the CCS 700 controls the first and second actuators 610 and 612 to position a selected group of linearly adjacent wells 34 at a target location beneath the linearly aligned drain tubes 558. More specifically, the CCS 700 moves the seed tray platform 602 within the X-Y coordinate system to position each of a plurality of linearly adjacent wells 34 beneath a corresponding one of the linearly aligned drain tubes 558. Therefore, when each of the seed gripping mechanisms 522 releases the respective sampled seeds, each sampled seed will fall, via gravity, vacuum or forced air, through the respective drain tube 558 into the corresponding well 34 located beneath the respective drain tube 558.

In operation, just prior to, simultaneously with, or just after the set of seeds is retained by the seed gripping mechanisms 522, as described above, the CCS 700 positions the selected well 34, or selected group of wells 34, at the target location. Each seed is then sampled and the samples are deposited in the sample tray wells 30, as described above. Each seed gripping mechanism 522 is commanded to release the respective seeds allowing the seeds to fall into the respective seed dump bowls 554. Each seed dump bowl 554 funnels the respective seeds through the respective drain port 556 and into the respective drain tubes 558. The drain tubes 558 then direct the respective seeds into the selected wells 34 positioned below the drain tubes 558. In various embodiments, the one or more of the seeds can be sequentially released and the seed tray platform 602 sequentially repositioned to deposit the one or more seeds into selected wells 34. In other embodiments, the seed tray platform is manipulated to position a group of linearly adjacent wells beneath the linearly aligned drain tubes, all the seeds are then substantially simultaneously released and deposited into the respective group of linearly adjacent wells.

As the seed trays 18 are placed on the seed tray platform 602, a tray identification number, e.g., a bar code, for each seed tray 18 and the location of each seed tray 18 on the seed tray platform 602 is recorded. Additionally, as each seed is deposited in a well 34, an X-Y location of the well on the seed tray platform 602 can be recorded. The recorded tray and well positions on the seed tray platform 602 can then be compared to the X-Y locations of each deposited seed, to map the specific seed in each well 34 of each seed tray 18. In various embodiments, the seed tray platform 602 is removably coupled to the X-Y stage 604 such that one or more seed tray platforms 602 can be loaded with the seed trays 18 offline, i.e., away from the seed sorter system 10, and conveniently coupled to and decoupled from the X-Y stage 604.

As described above, each of the seed trays 18 and the sample trays 14 include a plurality of wells 34 and 30, respectively. In various embodiments, the number and arrangement of the wells 34 in the seed trays 18 corresponds to the number and arrangement of the wells 30 in the sample trays 14. This facilitates a one-to-one correspondence between a seed and its extracted sample.

As described above, the sampling systems and methods of this disclosure protect germination viability of the seeds so as to be non-destructive. Germination viability means that a predominant number of sampled seeds (i.e., greater than 50% of all sampled seeds) remain viable after sampling. In some particular embodiments, at least about 75% of sampled seeds, and in some embodiments at least about 85% of sampled seeds remain viable. It should be noted that lower rates of germination viability may be tolerable under certain circumstances or for certain applications, for example, as genotyping costs decrease with time because a greater number of seeds could be sampled for the same genotype cost.

In yet other embodiments, germination viability is maintained for at least about six months after sampling to ensure that the sampled seed will be viable until it reaches the field for planting. In some particular embodiments, the methods of the present disclosure further comprise treating the sampled seeds to maintain germination viability. Such treatment may generally include any means known in the art for protecting a seed from environmental conditions while in storage or transport. For example, in some embodiments, the sampled seeds may be treated with a polymer and/or a fungicide to protect the sampled seed while in storage or in transport to the field before planting.

In various embodiments, the samples of the present disclosure are used in a high-throughput, non-destructive method for analyzing individual seeds in a population of seeds. The method comprises removing a sample from the seed while preserving the germination viability of the seed; and screening the sample for the presence or absence of one or more characteristics indicative of a genetic or chemical trait. The method may further comprise selecting seeds from the population based on the results of the screening; and cultivating plants from the selected seed.

Although the present disclosure exemplarily describes the high-throughput sampling of maize seeds, one skilled in the art would recognize that any seed can generally be utilized in a method or device of the present invention. For example, in various embodiments, the seed can be selected from the group consisting of alfalfa seed, apple seed, banana seed, barley seed, broccoli seed, cabbage seed, canola seed, carrot seed, castorbean seed, cauliflower seed, Chinese cabbage seed, citrus seed, clover seed, coconut seed, coffee seed, maize seed, cotton seed, cucumber seed, Douglas fir seed, dry bean seed, eggplant seed, Eucalyptus seed, fennel seed, garden bean seed, gourd seed, leek seed, lettuce seed, Loblolly pine seed, linseed seed, melon seed, oat seed, okra seed, olive seed, onion seed, palm seed, pea seed, peanut seed, pepper seed, poplar seed, pumpkin seed, Radiata pine seed, radish seed, rapeseed seed, rice seed, rye seed, spinach seed, sorghum seed, squash seed, Southern pine seed, soybean seed, strawberry seed, sugarbeet seed, sugarcane seed, sunflower seed, sweet corn seed, sweetgum seed, tea seed, tobacco seed, tomato seed, turf seed, watermelon seed, wheat seed, and *Arabidopsis thaliana* seed. In a more particular embodiment, the seed is selected from the group consisting of cotton seed, cucumber seed, maize seed, soybean seed, rapeseed seed, rice seed, okra seed, watermelon seed and wheat seed. In an even more particular embodiment, the seed is a maize seed, a cotton seed, a cucumber seed or a watermelon seed.

DNA may be extracted from the sample using any DNA extraction methods known to those of skill in the art which will provide sufficient DNA yield, DNA quality, and PCR response. A non-limiting example of suitable DNA-extraction methods is SDS-based extraction with centrifugation. In addition, the extracted DNA may be amplified after extraction using any amplification method known to those skilled in the art. For example, one suitable amplification method is the GenomiPhi® DNA amplification prep from Amersham Biosciences.

The extracted DNA is screened for the presence or absence of a suitable genetic marker. A wide variety of genetic markers are available and known to those of skill in the art. The DNA screening for the presence or absence of the genetic marker can be used for the selection of seeds in a breeding population. The screening may be used to select for QTL, alleles, or genomic regions (haplotypes). The alleles, QTL, or haplotypes to be selected for can be identified using newer techniques of molecular biology with modifications of classical breeding strategies.

In other various embodiments, the seed is selected based on the presence or absence of a genetic marker that is genetically linked with a QTL. Examples of QTLs which are often of interest include but are not limited to yield, lodging resistance, height, maturity, disease resistance, pest resistance, resistance to nutrient deficiency, grain composition, herbicide tolerance, fatty acid content, protein or carbohydrate metabolism, increased oil content, increased nutritional content, stress tolerance, organoleptic properties, morphological characteristics, other agronomic traits, traits for industrial uses, traits for improved consumer appeal, and a combination of traits as a multiple trait index. Alternatively, the seed can be selected based on the presence or absence of a marker that is genetically linked with a haplotype associated with a QTL. Examples of such QTL may again include, without limitation, yield, lodging resistance, height, maturity, disease resistance, pest resistance, resistance to nutrient deficiency, grain composition, herbicide tolerance, fatty acid content, protein or carbohydrate metabolism, increased oil content, increased nutritional content, stress tolerance, organoleptic properties, morphological characteristics, other agronomic traits, traits for industrial uses, traits for improved consumer appeal, and a combination of traits as a multiple trait index.

Selection of a breeding population could be initiated as early as the $F_2$ breeding level, if homozygous inbred parents are used in the initial breeding cross. An $F_1$ generation could also be sampled and advanced if one or more of the parents of the cross are heterozygous for the alleles or markers of interest. The breeder may screen an $F_2$ population to retrieve the marker genotype of every individual in the population. Initial population sizes, limited only by the number of available seeds for screening, can be adjusted to meet the desired probability of successfully identifying the desired number of individuals. See Sedcole, J. R. "Number of plants necessary to recover a trait." *Crop Sci.* 17:667-68 (1977). Accordingly, the probability of finding the desired genotype, the initial population size, and the targeted resulting population size can be modified for various breeding methodologies and inbreeding level of the sampled population.

The selected seeds may be bulked or kept separate depending on the breeding methodology and target. For example, when a breeder is screening an $F_2$ population for disease resistance, all individuals with the desired genotype may be bulked and planted in the breeding nursery. Conversely, if multiple QTL with varying effects for a trait such as grain yield are being selected from a given population, the breeder may keep individual identity preserved, going to the field to differentiate individuals with various combinations of the target QTL.

Several methods of preserving single seed identity can be used while transferring seed from a sampling facility to the field. Methods include, but are not limited to, transferring selected individuals to seed tape, a cassette tray, or indexing tray, transplanting with peat pots, and hand-planting from individual seed packets. Multiple cycles of selection can be utilized depending on breeding targets and genetic complexity.

The screening methods of the disclosure may further be used in a breeding program for introgressing a trait into a plant. Such methods comprise removing a sample comprising cells with DNA from seeds in a population, screening the DNA extracted from each seed for the presence or absence of at least one genetic marker, selecting seeds from the population based upon the results of the DNA screening; cultivating a fertile plant from the seed; and utilizing the fertile plant as either a female parent or male parent in a cross with another plant.

Examples of genetic screening to select seeds for trait integration include, without limitation, identification of high recurrent parent allele frequencies, tracking of transgenes of interest or screening for the absence of unwanted transgenes, selection of hybrid testing seed, and zygosity testing.

The identification of high recurrent pair allele frequencies via the screening methods of the present disclosure again allows for a reduced number of rows per population and an increased number of populations, or inbred lines, to be planted in a given field unit. Thus, the screening methods of the present disclosure may also effectively reduce the resources required to complete the conversion of inbred lines.

The methods of the present disclosure further provide quality assurance (QA) and quality control by assuring that regulated or unwanted transgenes are identified and discarded prior to planting.

The methods of the present disclosure may be further applied to identify hybrid seed for transgene testing. For example, in a conversion of an inbred line at the $BCnF_1$ stage, a breeder could effectively create a hybrid seed lot (barring gamete selection) that was 50% hemizygous for the trait of interest and 50% homozygous for the lack of the trait in order to generate hybrid seed for testing. The breeder could then screen all $F_1$ seeds produced in the test cross and identify and select those seeds that were hemizygous. Such method is advantageous in that inferences from the hybrid trials would represent commercial hybrid genetics with regard to trait zygosity.

Other applications of the screening methods of this disclosure for identifying and tracking traits of interest carry the same advantages identified above with respect to required field and labor resources. Generally, transgenic conversion programs are executed in multi-season locations which carry a much higher land and management cost structure. As such, the impact of either reducing the row needs per population or increasing the number of populations within a given field unit are significantly more dramatic on a cost basis versus temperate applications.

Still further, the screening methods of this disclosure may be used to improve the efficiency of the doubled haploid program through selection of desired genotypes at the haploid stage and identification of ploidy level to eliminate non-haploid seeds from being processed and advancing to the field. Both applications again result in the reduction of field resources per population and the capability to evaluate a larger number of populations within a given field unit.

In various embodiments, the disclosure further provides an assay for predicting embryo zygosity for a particular gene of interest (GOI). The assay predicts embryo zygosity based on the ratio of the relative copy numbers of a GOI and of an internal control (IC) gene per cell or per genome. Generally, this assay uses an IC gene that is of known zygosity, e.g., homozygous at the locus (two IC copies per diploid cell), for normalizing measurement of the GOI. The ratio of the relative copy numbers of the IC to the GOI predicts the GOI copy number in the cell. In a homozygous cell, for any given gene (or unique genetic sequence), the gene copy number is equal to the cell's ploidy level since the sequence is present at the same locus in all homologous chromosomes. When a cell is heterozygous for a particular gene, the gene copy number will be lower than the cell's ploidy level. The zygosity of a cell at any locus can thus be determined by the gene copy number in the cell.

In some particular embodiments, the disclosure provides an assay for predicting corn embryo zygosity. In corn seed, the endosperm tissue is triploid, whereas the embryo tissue is diploid. Endosperm that is homozygous for the IC will contain three IC copies. Endosperm GOI copy number can range from 0 (homozygous negative) to 3 (homozygous positive); and endosperm GOI copy number of 1 or 2 is found in seed heterozygous for the GOI (or hemizygous for the GOI if the GOI is a transgene). Endosperm copy number is reflective of the zygosity of the embryo: a homozygous (positive or negative) endosperm accompanies a homozygous embryo, heterozygous endosperm (whether a GOI copy number of 1 or 2) reflects a heterozygous (GOI copy number of 1) embryo. The endosperm GOI copy number (which can range from 0 to 3 copies) can be determined from the ratio of endosperm IC copy number to endosperm GOI copy number (which can range from 0/3 to 3/3, that is, from 0 to 1), which can then be used to predict zygosity of the embryo.

Copy numbers of the GOI or of the IC can be determined by any convenient assay technique for quantification of copy numbers, as is known in the art. Examples of suitable assays include, but are not limited to, Real Time (TaqMan®) PCR (Applied Biosystems, Foster City, Calif.) and Invader® (Third Wave Technologies, Madison, Wis.) assays. Preferably, such assays are developed in such a way that the amplification efficiency of both the IC and GOI sequences are equal or very similar. For example, in a Real Time TaqMan® PCR assay, the signal from a single-copy GOI (the source cell is determined to be heterozygous for the GOI) will be detected one amplification cycle later than the signal from a two-copy IC, because the amount of the GOI is half that of the IC. For the same heterozygous sample, an Invader® assay would measure a GOI/IC ratio of about 1:2 or 0.5. For a sample that is homozygous for both the GOI and the IC, the GOI signal would be detected at the same time as the IC signal (TaqMan®), and the Invader assay would measure a GOI/IC ratio of about 2:2 or 1.

These guidelines apply to any polyploid cell, or to haploid cells (such as pollen cells), since the copy number of the GOI or of the IC remain proportional to the genome copy number (or ploidy level) of the cell. Thus, these zygosity assays can be performed on triploid tissues such as corn endosperm.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. An automated method for removing tissue from seeds using a seed sampling system, the method comprising:
   determining, by a control system in communication with the seed sampling system, at least one characteristic of a seed isolated from a bulk of seeds;
   adjusting, by the control system, operation of a sampling subsystem of the seed sampling system based on the at least one characteristic of the seed; and
   removing tissue from the seed at the sampling subsystem.

2. The method of claim 1, further comprising isolating the seed from the bulk of seeds.

3. The method of claim 1, further comprising:
   receiving the tissue removed from the seed in a sample tray and mapping a location of the tissue in the sample tray; and/or
   receiving the seed from which the tissue is removed in a seed tray and mapping a location of the seed in the seed tray.

4. The method of claim 1, further comprising collecting the tissue removed from the seed and correlating the collected tissue to the seed.

5. The method of claim 4, further comprising screening the tissue removed from the seed.

6. The method of claim 1, wherein the at least one characteristic includes size of the seed; and
   wherein adjusting operation of the sampling subsystem of the seed sampling system includes adjusting operation of the sampling subsystem based on the size of the seed so that a predetermined amount of tissue is removed from the seed at the sampling subsystem.

7. A high-throughput, automated method for use in analyzing seeds, the method comprising:
   determining, by a control system in communication with a seed sampling system, at least one characteristic of each of multiple individual seeds;
   removing tissue from each of the individual seeds using a sampling subsystem of the seed sampling system; and
   prior to removing the tissue from each of the individual seeds, adjusting, by the control system, at least one operational parameter of the sampling subsystem based on the at least one characteristic of the seed from which the tissue is to be removed.

8. The method of claim 7, further comprising isolating the multiple individual seeds from a bulk of seeds.

9. The method of claim 7, further comprising:
receiving the tissue removed from the seeds in a sample tray and mapping locations of the tissue in the sample tray; and/or
receiving the seeds from which the tissue is removed in a seed tray and mapping locations of the seeds in the seed tray.

10. The method of claim 7, further comprising collecting the tissue removed from the seeds and correlating the collected tissue to the seeds from which it was removed.

11. The method of claim 10, further comprising analyzing the tissue removed from the seeds for presence or absence of at least one characteristic.

12. The method of claim 11, further comprising selecting desired ones of the individual seeds based on presence or absence of the at least one characteristic.

13. The method of claim 7, wherein the at least one characteristic of each of the individual seeds includes size of the seeds; and
wherein adjusting at least one operational parameter of the sampling subsystem includes adjusting operation of one or more cutting devices of the sampling subsystem based on the size of the seed from which the tissue is to be removed so that generally equal amounts of tissue are removed from each of the multiple individual seeds.

14. The method of claim 13, wherein adjusting operation of one or more cutting devices of the sampling subsystem based on the size of the seed from which the tissue is to be removed includes adjusting an angular rotation of the one or more cutting devices based on the size of the seed from which the tissue is to be removed.

15. An automated seed sampling system for use in removing tissue from seeds, the system comprising:
a sampling subsystem configured to remove tissue from each of a plurality of seeds; and
a control system in communication with the sampling subsystem, the control system configured, for each of the plurality of seeds, to:
determine at least one characteristic of the seed; and
adjust at least one operational parameter of the sampling subsystem based on the at least one characteristic of the seed, prior to removal of the tissue from the seed by the sampling subsystem.

16. The system of claim 15, wherein the at least one characteristic of the seed includes size of the seed; and
wherein the control system is configured, in connection with adjusting the at least one operational parameter of the sampling subsystem, to adjust operation of one or more cutting devices of the sampling subsystem based on the size of the seed.

17. The system of claim 16, wherein the control system is configured, in connection with adjusting operation of the one or more cutting devices of the sampling subsystem, to adjust an angular rotation of the one or more cutting devices based on the size of the seed.

18. The system of claim 15, further comprising an imaging station in communication with the control system, the imaging station configured to collect image data from each of the plurality of seeds; and
wherein the control system is further configured, for each of the plurality of seeds, to determine the at least one characteristic of the seed based on the collected image data.

19. The system of claim 15, wherein the control system is further configured, for each of the plurality of seeds, to:
direct the tissue removed from the seed to a sample tray and map a location of the tissue in the sample tray; and/or
direct the seed from which the tissue is removed to a seed tray and map a location of the seed in the seed tray.

* * * * *